US008287869B2

(12) United States Patent
Gurney

(10) Patent No.: US 8,287,869 B2
(45) Date of Patent: *Oct. 16, 2012

(54) METHOD OF TREATING INFLAMMATORY DISEASE BY INHIBITION OF IL-17 PRODUCTION

(75) Inventor: Austin L. Gurney, Belmont, CA (US)

(73) Assignee: Genentech, Inc., South San Francisco, CA (US)

(*) Notice: Subject to any disclaimer, the term of this patent is extended or adjusted under 35 U.S.C. 154(b) by 276 days.

This patent is subject to a terminal disclaimer.

(21) Appl. No.: 12/350,125

(22) Filed: Jan. 7, 2009

(65) Prior Publication Data

US 2010/0266583 A1 Oct. 21, 2010

Related U.S. Application Data

(62) Division of application No. 10/697,599, filed on Oct. 29, 2003, now Pat. No. 7,510,709.

(60) Provisional application No. 60/423,090, filed on Oct. 30, 2002.

(51) Int. Cl.
*A61K 39/395* (2006.01)
*C12P 21/08* (2006.01)

(52) U.S. Cl. .................. 424/145.1; 530/388.23

(58) Field of Classification Search .................. None
See application file for complete search history.

(56) References Cited

U.S. PATENT DOCUMENTS

| 6,060,284 A | 5/2000 | Bazan | 435/69.52 |
|---|---|---|---|
| 6,479,634 B1 | 11/2002 | Bazan | 530/351 |
| 6,495,667 B1 | 12/2002 | Bazan | 530/389.2 |
| 6,610,285 B1 | 8/2003 | Hirata | 424/85.1 |
| 6,756,481 B2 | 6/2004 | Chirica et al. | 530/387.9 |
| 6,835,825 B1 | 12/2004 | Bazan | 536/24.31 |
| RE39,015 E | 3/2006 | Bazan | 435/69.52 |
| 2003/0009018 A1 | 1/2003 | Maeda et al. | 536/23.1 |
| 2003/0082734 A1 | 5/2003 | Dowling et al. | 435/69.1 |
| 2003/0124123 A1 | 7/2003 | Giles-Komar et al. | 424/145.1 |
| 2004/0223969 A1 | 11/2004 | Oft et al. | 424/145.1 |
| 2004/0258686 A1 | 12/2004 | Chirica et al. | 424/143.1 |
| 2005/0004354 A1* | 1/2005 | Salfeld et al. | 530/388.23 |
| 2005/0100917 A1 | 5/2005 | Chirica et al. | 435/6 |
| 2005/0100918 A1 | 5/2005 | Chirica et al. | 435/6 |
| 2005/0158750 A1 | 7/2005 | Bazan | 435/6 |
| 2005/0208052 A1 | 9/2005 | Katsikis et al. | 424/145.1 |
| 2005/0250770 A1 | 11/2005 | Ono et al. | 514/227.8 |
| 2005/0250774 A1 | 11/2005 | Ono et al. | 514/235.2 |
| 2005/0287593 A1 | 12/2005 | Kastelein et al. | 435/6 |
| 2006/0067936 A1 | 3/2006 | Benson et al. | 424/145.1 |

FOREIGN PATENT DOCUMENTS

| WO | WO 99/05280 | 2/1999 |
|---|---|---|
| WO | WO 00/56772 | 9/2000 |
| WO | WO 01/18022 | 3/2001 |
| WO | WO 01/18051 | 3/2001 |
| WO | WO 01/85790 | 11/2001 |
| WO | WO 02/12500 | 2/2002 |
| WO | WO 2005/046604 | 5/2005 |
| WO | WO 2005/108616 | 11/2005 |

OTHER PUBLICATIONS

Aarvak, T., et al., *Scandinavian Journal of Immunology*—50: No. 1-9 (1999) (XP-002352889).
Belladonna, M.L., et al., *The Journal of Immunology*—168:5448-5454 (2002).
Benson, J., et al., *The FASEB Journal*—16(5): p. A1045, Abstract #759.12 (Mar. 22, 2002).
Bowman, E.P., et al., *Current Opinion in Infectious Diseases*—19:245-252 (2006).
Brok, H.P. M, et al., *The Journal of Immunology*—169:6554-6563 (2002) (XP-002971968).
Frucht, D.M., *Science STKE*—114:1-3 (2002).
Kotake, S., et al., *Journal of Clinical Investigation*—103(9):1345-1352 (1999).
Maeyama, T., et al., *American Journal of Physiology, Lung Cellular and Molecular Physiology*—280(6):L1128-L1137 (2001) (XP-002352888).
Matusevicius, D., et al., *Multiple Sclerosis*—5(2):101-104 (1999).
Oppmann, B., et al., *Immunity*—13(5):715-725 (2000).
Parham, C., et al., *Journal of Imunology*—168:5699-5708 (2002).
Tripp, C.S., et al., *Journal of Immunology*—152:1883-1887 (1994) (XP-002924062).
Wiekowski, M.T., et al., *Journal of Immunology*—166:7563-7570 (2001).
Wong, C.K., et al., *Lupus*—9:589-593 (2000).
Zhang, Z., et al., *Interntional Imunopharmacology*—7:409-416 (2007).
(Exhibit SGT-1 referred to in the Statutory declaration by Stuart Graham Tangye dated Dec. 3, 2010.) Curriculum Vitae for Dr. Stuart G. Tangye. (Exhibit SGT-2 referred to in the Statutory declaration by Stuart Graham Tangye dated Dec. 3, 2010.) Mosmann, et al., "Two types of murine helper t cell clone", The Journal of Immunology, vol. 136, No. 7, pp. 2348-2357, (1986).
(Exhibit SGT-3 referred to in the Statutory declaration by Stuart Graham Tangye dated Dec. 3, 2010.) Fiorentino, et al., "Two types of mouse T helper cell IV. Th2 clones secrete a factor that inhibits cytokine production by Th1 clones", J. Exp. Med., vol. 170, pp. 2081-2095, (1989).
(Exhibit SGT-4 referred to in the Statutory declaration by Stuart Graham Tangye dated Dec. 3, 2010.) Moore, et al., "Homology of cytokine synthesis inhibitory factor (IL-10) to the epstein-Barr virus gene BCRFI", Science, vol. 248, pp. 1230-1234, (1990).
(Exhibit SGT-5 referred to in the Statutory declaration by Stuart Graham Tangye dated Dec. 3, 2010.) Jovanovic, et al., "IL-17 stimulates the production and expression of proinflammatory cytokines, Il-β and TNFα, by human macrophages", The Journal of Immunology, 160: 3513-3521, (1998).
(Exhibit SGT-6 referred to in the Statutory declaration by Stuart Graham Tangye dated Dec. 3, 2010.) Lubberts, et al., "IL-4 gene therapy for collagen arthritis suppresses synovial IL-17 and osteoprotegerin ligand and prevents bone erosion", The Journal of Clinical Investigation, vol. 105, No. 12, pp. 1697-1710, (2000).
(Exhibit SGT-7 referred to in the Statutory declaration by Stuart Graham Tangye dated Dec. 3, 2010.) Schreiber, et al., "Tumour necrosis factor α and interleukin 1β in relapse of Crohn's disease", The Lancet, vol. 353, 459-461, (1999).

(Continued)

*Primary Examiner* — Robert Landsman
*Assistant Examiner* — Bruce D Hissong
(74) *Attorney, Agent, or Firm* — Bonny Yeung; Ginger R. Dreger; Arnold & Porter LLP

(57) ABSTRACT

The invention concerns inhibition of the production of proinflammatory cytokine interleukin-17 (IL-17) by T cells, using an antagonist of interleukin-23 (IL-23). The invention further concerns the use of IL-23 antagonists in the treatment of inflammatory diseases characterized by the presence of elevated levels of IL-17. IL-23 antagonists include, without limitation, antibodies specifically binding to a subunit or IL-17 or an IL-17 receptor. The invention additionally concerns induction of IL-7 production by using an IL-23 agonist.

10 Claims, 9 Drawing Sheets

OTHER PUBLICATIONS (Exhibit SGT-8 referred to in the Statutory declaration by Stuart Graham Tangye dated Dec. 3, 2010.) Funakoshi, et al., "Spectrum of cytokine gene expression in intestinal mucosal lesions of Crohn's disease and ulcerative colitis", Digestion, 59: 73-78, (1998).
(Exhibit SGT-20 referred to in the Statutory declaration by Stuart Graham Tangye dated Dec. 3, 2010.) Kobayashi, et al., "Identification and purification of natural killer cell stimulatory factor (NKSF), A cytokine with multiple biologic effects on human lymphocytes", J. Exp. Med., vol. 170, pp. 827-845, (1989).
(Exhibit SGT-21 referred to in the Statutory declaration by Stuart Graham Tangye dated Dec. 3, 2010.) Manetti, et al., "Natural killer cell stimulatory factor (Interleukin 12 [IL-12]) induces T helper type 1 (Th1)-specific immune responses and inhibits the development of IL-4-producing Th cells", J. Exp. Med., vol. 177, 1199-1204, (1993).
(Exhibit SGT-22 referred to in the Statutory declaration by Stuart Graham Tangye dated Dec. 3, 2010.) Sornasse, et al., "Differentiation and stability of T helper 1 and 2 cells derived from naïve human neonatal CD4 T cells, analyzed at the single-cell level", J. Exp. Med, vol. 184, 473-483, (1996).
(Exhibit SGT-23 referred to in the Statutory declaration by Stuart Graham Tangye dated Dec. 3, 2010.) Gately, et al., "The interleukin-12/interleukin-12-receptor system: Role in normal and pathologic immune responses", Annu. Rev. Immunol , 16: 495-521, (1998).
(Exhibit SGT-24 referred to in the Statutory declaration by Stuart Graham Tangye dated Jun. 28, 2011.) Fort, et al., "IL-25 induces Il-4, IL-5 and IL-13 and Th2-associated pathologies in vivo", Immunity, vol. 15, 985-995, (2001).
(Exhibit SGT-25 referred to in the Statutory declaration by Stuart Graham Tangye dated Jun. 28, 2011.) Starnes, et al., "Cutting edge: IL-17F, a novel cytokine selectively expressed in activated T cells and monocytes, regulates angiogenesis and endothelial cell cytokine production", The Journal of Immunology, 167: 4137-4140, (2001).
(Exhibit SGT-26 referred to in the Statutory declaration by Stuart Graham Tangye dated Jun. 28, 2011.) Hurst, et al., "New IL-17 family members promote Th1 or Th2 responses in the lung: In vivo function of the novel cytokine Il-25", The Journal of Immunology, 169: 443-453, (2002).
(Exhibit SGT-27 referred to in the Statutory declaration by Stuart Graham Tangye dated Jun. 28, 2011.) Lee, et al., "IL-17E, A Novel proinflammatory ligand for the IL-17 receptor homolog IL-17Rh1", The Journal of Biological Chemistry, vol. 276, No. 2, 1660-1664, (2001).
(Exhibit SGT-28 referred to in the Statutory declaration by Stuart Graham Tangye dated Jun. 28, 2011.) Li, et al., "Cloning and characterization of IL-17B and IL-17C, two new members of the IL-17 cytokine family", PNAS, vol. 97, No. 2, 773-778, (2000).
Aggarwal, et al., "Interleukin-23 promotes a distinct CD4 T cell activation state characterized by the production of Interleukin-17", the Journal of Biological Chemistry, vol. 278, No. 3, pp. 1910-1914, (2003).
Arican, et al., "Serum levels of TNF-α, IFN-γ, IL-6, IL-8, IL-12, IL-17, and IL-18 in patients with active psoriasis and correlation with disease severity", Mediators of Inflammation, 5: 273-279, (2005).
Becher, et al., "Experimental autoimmune encephalitis and inflammation in the absence of interleukin-12", The Journal of Clinical Investigation—110(4): 493-497 (2002).
Chabaud et al., "Human Interleukin-17: A T Cell-Derived Proinflammatory Cytokine Produced by the Rheumatoid Synovium" Arthritis & Rheumatism 42(5): 963-970, (1999).
Constantinescu, et al., "Antibodies against IL-12 prevent superantigen-induced and spontaneous relapses of experimental autoimmune encephalomyelitis", The Journal of Immunology, 161: 5097-5104 (1998).
Frisullo, et al., "IL-17 and IFN-γ production by peripheral blood mononuclear cells from clinically isolated syndrome to secondary progressive multiple sclerosis", Cytokine, 44: 22-25, (2008).
Fujino, et al., "Increased expression of interleukin 17 inflammatory bowel disease", Gut, 52: 65-70, (2003).
Ghilardi, et al., "Comprised humoral delayed-type hypersensitivity responses in IL-23-deficient mice", The Journal of Immunology, 172: 2827-2833, (2004).

Hamzaoui, et al., "Cytokine profile in Behcet's disease patients", Scand. J. Rheumatol, 31: 205-210, (2002).
Kagami, et al., "Circulating Th17, Th22, and Th1 cells are increased in psoriasis", Journal of Investigative Dermatology, 130: 1373-1383, (2010).
Katsifis, et al., "Systemic and local interleukin-17 and linked cytokines associated with Sjogren's syndrome immunopathogenesis", The American journal of Immunology, vol. 175, No. 3, 1167-1177, (2009).
Kikly, et al., "Thw Il-23/Th$_{17}$ axis: therapeutic targets for autoimmune inflammation", Current opinion in Immunology, 18: 670-675, (2006).
Kullberg, et al., "Helicobacter hepaticus-induced colitis in interleukin-10-deficient mice: Cytokine requirements for the induction and maintenance of intestinal inflammation", Infection and Immunity, pp. 4232-4241, (2001).
Kurasawa et al., "Increased interleukin-17 production in patients with systemic sclerosis" Arthritis and Rheumatism 43(11):2455-2463, (2000).
Lankford, et al., "A unique folc for IL-23 in promoting cellular immunity", Journal of Leukocyte Biology, vol. 73, 49-56, (2003).
Lo, et al., "Antitumor and Antimetastatic activity if IL-23", The Journal of Immunology, 171: 600-607, (2003).
Molet, et al., "IL-17 is increased in asthmatic airways and induces human bronchial fibroblasts to produce cytokines", J. Allergy Clin. Immunol., 108: 430-438, (2001).
Neurath, et al., "Antibodies to interleukin 12 abrogate established experimental colitis in mice", The Journal of Experimental Medicine, vol. 182, pp. 1281-1290, (1995).
Shen, et al., "Frequency and phenotype of peripheral blood Th17cells in ankylosing spondylitis and rheumatoid arthritis", Arthritis & Rheumatism, vol. 60, No. 6, pp. 1647-1656, (2009).
Statutory Declaration by Stuart Graham Tangye dated Dec. 3, 2010.
Statutory Declaration by Stuart Graham Tangye dated Jun. 28, 2011.
Statutory Declaration by Stuart Graham Tangye dated Sep. 28, 2011.
Wong, et al., "Proinflammatory cytokines (IL-17, IL-6, IL-18 and IL-12) and Th cytokines (IFN-γ, IL-4, IL-10 and IL-13) in patients with allergic asthma", Clinical Exp. Immunology, 125: 177-183, (2001).
Wysocka, et al., "Interleukin-12 is required for interferon-γ production and lethality in lipopolysaccharide-induced shock in mice", Eur. J. Imm., 25: 672-676, (1995).
Zhao, et al., "Increased serum interleukin 17 in patients with systemic lupus erythematosus", Mol. Biol. Rep., 37: 81-85, (2010).
(Exhibit SGT-9 referred to in the Statutory declaration by Stuart Graham Tangye dated Dec. 3, 2010.) Feldman, et al., "Role of cytokines in rheumatoid arthritis", Annu. Rev. Immunol., 14: 397-440, (1996).
(Exhibit SGT-10 referred to in the Statutory declaration by Stuart Graham Tangye dated Dec. 3, 2010.) Desai-Mehta, et al., "Hyper expression of CD40 ligand by B and T cells in human lupus and its role in pathogenic autoantibody production", J. Clin. Invest., 97: 2063-2073, (1996).
(Exhibit SGT-11 referred to in the Statutory declaration by Stuart Graham Tangye dated Dec. 3, 2010.) Kato, et al., "The soluble CD40 ligand sCD154 in systemic lupus erythematosus", The Journal of Clinical Investigation, vol. 104, No. 7, pp. 947-955, (1999).
(Exhibit SGT-12 referred to in the Statutory declaration by Stuart Graham Tangye dated Dec. 3, 2010.) Sorensen, et al., "Expression of specific chemokines and chemokine receptors in the central nervous system of multiple sclerosis patients", The Journal of Clinical Investigation, vol. 103, No. 6, pp. 807-815, (1999).
(Exhibit SGT-13 referred to in the Statutory declaration by Stuart Graham Tangye dated Dec. 3, 2010.) Mahad, et al., "Expression of chemokines in the CSF and correlation with clinical disease activity in patients with multiple sclerosis", J. Neurol Neurosurg. Psychiatry, 72: 498-502, (2002).
(Exhibit SGT-14 referred to in the Statutory declaration by Stuart Graham Tangye dated Dec. 3, 2010.) Boven, et al., "Macrophage inflammatory protein-1α (MIP-1α), MIP-1β, and RANTES mRNA semiquantification and protein expression in active demyelinating multiple sclerosis (MS) lesions", Clin. Exp. Immunol., 122: 257-263, (2000).

(Exhibit SGT-15 referred to in the Statutory declaration by Stuart Graham Tangye dated Dec. 3, 2010.) Abramson, et al., "Blocking the effects of IL-1 in rheumatoid arthritis protects bone and cartilage", Rheumatology, 41: 972-980, (2002).

(Exhibit SGT-16 referred to in the Statutory declaration by Stuart Graham Tangye dated Dec. 3, 2010.) Feldmann, et al., "Anti-TNFα therapy of rheumatoid arthritis: What have we learned?", Annu. Rev. Immunol, 19: 163-196, (2001).

(Exhibit SGT-17 referred to in the Statutory declaration by Stuart Graham Tangye dated Dec. 3, 2010.) Llorente, et al., "Clinical and biological effects of anti-interleukin-10 monoclonal antibody administration in systemic lupus erythematosus", Arthritis & Rheumatism, vol. 43, No. 8, pp. 1790-1800, (2000).

(Exhibit SGT-18 referred to in the Statutory declaration by Stuart Graham Tangye dated Dec. 3, 2010.) Hsieh, et al., "Development of $T_H1$ $CD4^+$ T cells through IL-12 produced by listeria-induced macrophages", Science, vol. 260, pp. 547-549, (1993).

(Exhibit SGT-19 referred to in the Statutory declaration by Stuart Graham Tangye dated Dec. 3, 2010.) Wolf, et al., "Cloning of cDNA for natural killer cell stimulatory factor, a heterodimeric cytokine with multiple biologic effects on T and natural killer cells", The Journal of Immunology, vol. 146, No. 9, pp. 3074-3081, (1991).

* cited by examiner

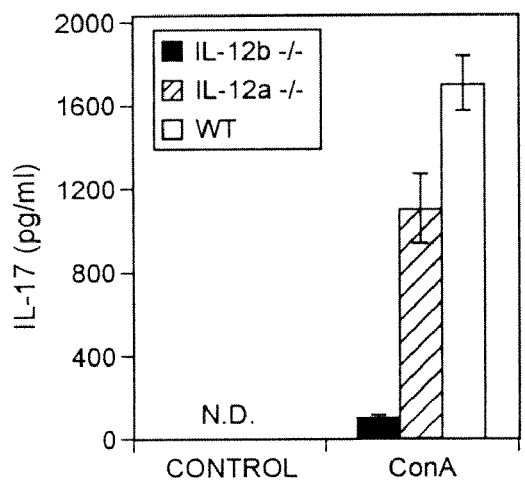
FIG. 4B
FIG. 5A
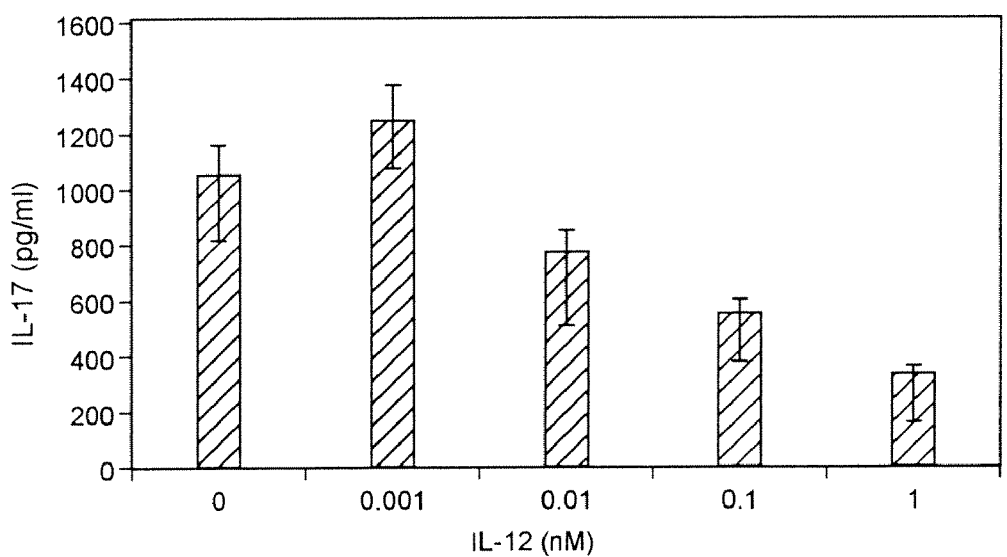
FIG. 5B
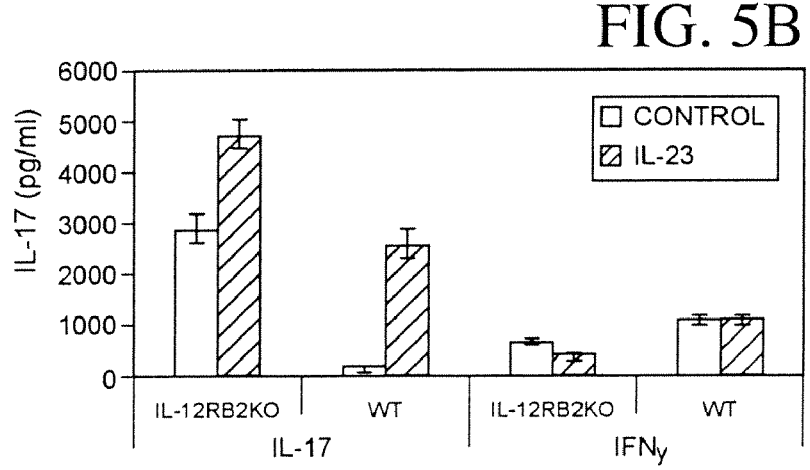

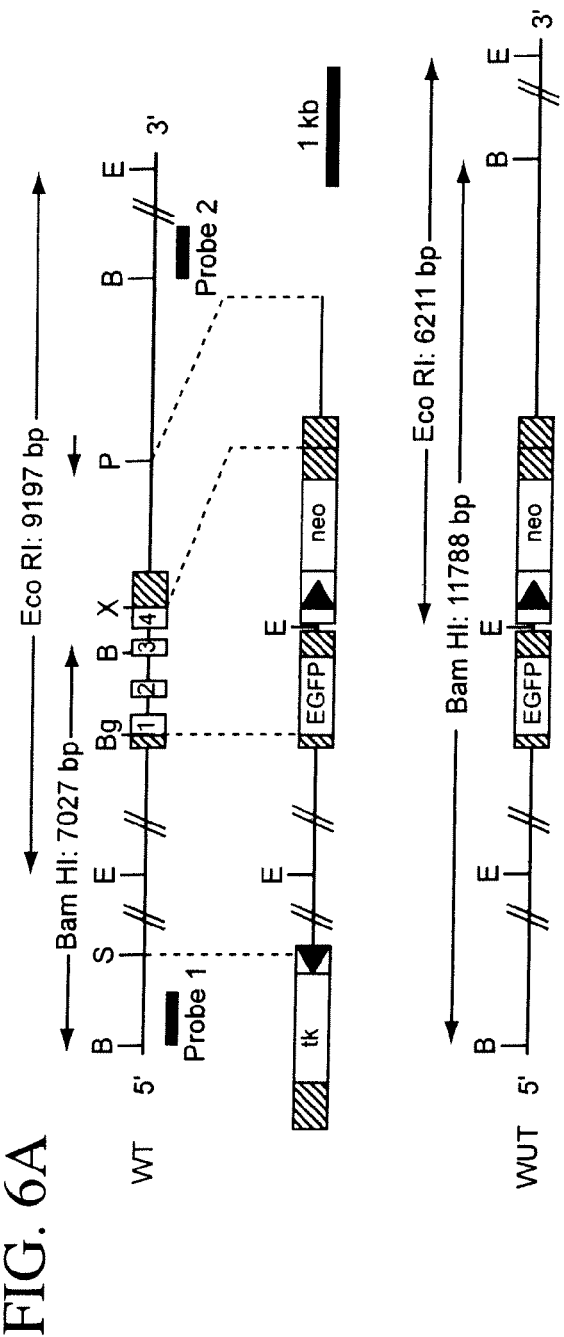
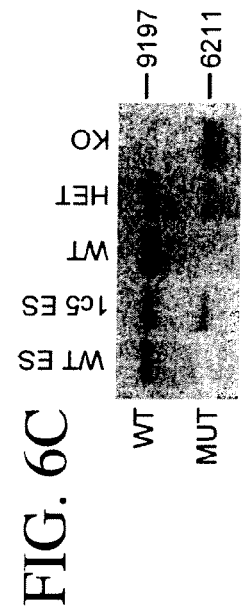
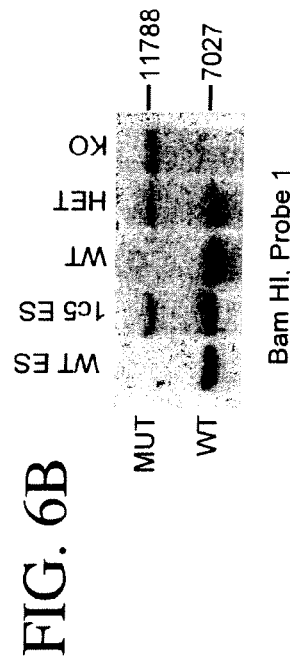
FIG. 6A
FIG. 6B
FIG. 6C

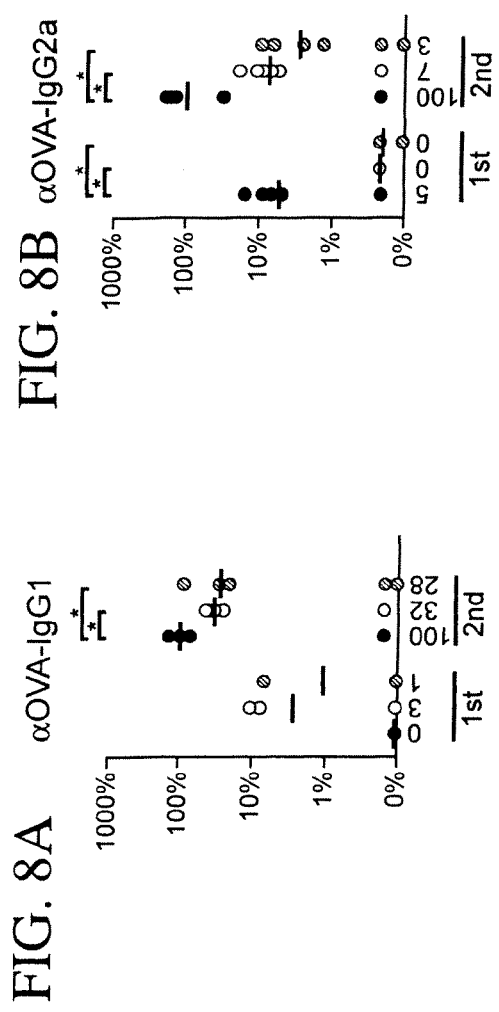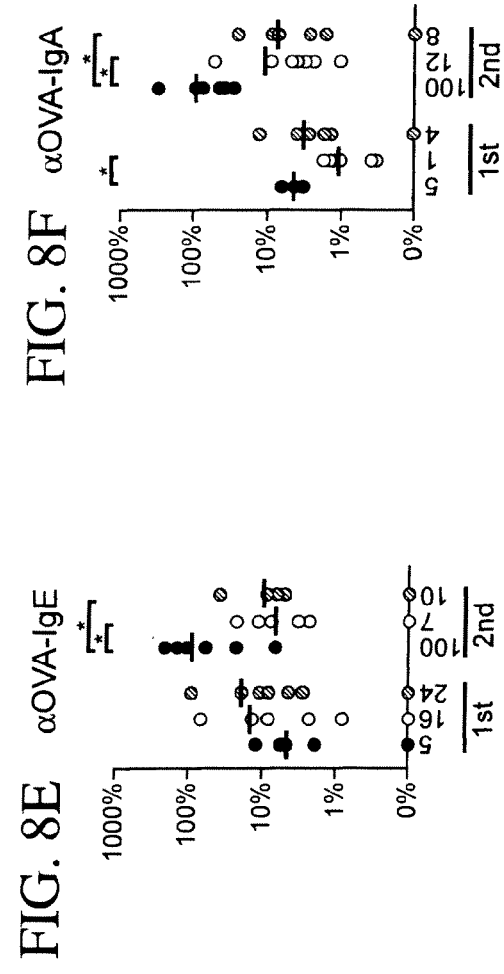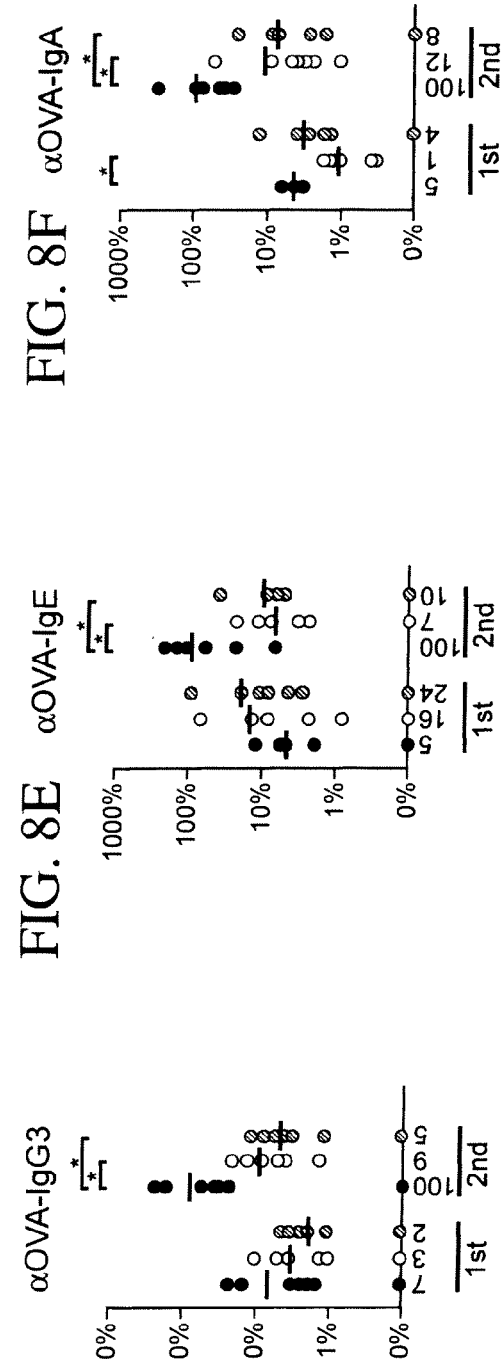
FIG. 8A αOVA-IgG1  FIG. 8B αOVA-IgG2a  FIG. 8C αOVA-IgG2b
FIG. 8D αOVA-IgG3  FIG. 8E αOVA-IgE   FIG. 8F αOVA-IgA

METHOD OF TREATING INFLAMMATORY DISEASE BY INHIBITION OF IL-17 PRODUCTION

CROSS-REFERENCE TO RELATED APPLICATIONS

This application is a divisional of, and claims priority under 35 U.S.C. §120 to, U.S. patent application Ser. No. 10/697,599, filed Oct. 29, 2003, now U.S. Pat. No. 7,510,709, which claims priority under U.S.C. §119(e) to U.S. Provisional Patent Application Ser. No. 60/423,090 filed Oct. 30, 2002, the disclosures of which are incorporated herein by reference in their entirety.

BACKGROUND OF THE INVENTION

1. Field of the Invention

The present invention concerns inhibition of the production of proinflammatory cytokine interleukin-17 (IL-17) by T cells, using an antagonist of interleukin-23 (IL-23). The invention further concerns the use of IL-23 antagonists in the treatment of inflammatory diseases characterized by the presence of elevated levels of IL-17.

2. Description of the Related Art

IL-17 is a T cell derived pro-inflammatory molecule that stimulates epithelial, endothelial and fibroblastic cells to produce other inflammatory cytokines and chemokines including IL-6, IL-8, G-CSF, and MCP-1 (S. Aggarwal, A. L. Gurney, *J Leukoc Biol* 71, 1 (2002); Z. Yao et al., *Immunity* 3, 811 (1995); J. Kennedy et al., *J Interferon Cytokine Res* 16, 611 (1996); F. Fossiez et al., *J Exp Med* 183, 2593 (1996); A. Linden, H. Hoshino, M. Laan, *Eur Respir J* 15, 973 (2000); X. Y. Cai, C. P. Gommoll, Jr., L. Justice, S. K. Narula, J. S. Fine, *Immunol Lett* 62, 51 (1998); D. V. Jovanovic et al., *J Immunol* 160, 3513 (1998); and M. Laan et al., *J Immunol* 162, 2347 (1999)).

IL-17 also synergizes with other cytokines including TNF-α and IL-1β to further induce chemokine expression (Jovanovic et al., supra, and M. Chabaud, F. Fossiez, J. L. Taupin, P. Miossec, *J Immunol* 161, 409 (1998)). Levels of IL-17 are found to be significantly increased in rheumatoid arthritis (RA) synovium (S. Kotake et al., *J Clin Invest* 103, 1345 (1999); and M. Chabaud et al., *Arthritis Rheum* 42, 963 (1999)), during allograft rejection (M. A. Antonysamy et al., *Transplant Proc* 31 (1999); M. A. Antonysamy et al., *J Immunol* 162, 577 (1999); C. C. Loong, C. Y. Lin, W. Y. Lui, *Transplant Proc* 32 (2000); and H. G. Hsieh, C. C. Loong, W. Y. Lui, A. Chen, C. Y. Lin, *Transpl Int* 14, 287 (2001)), and in other chronic inflammatory diseases including multiple sclerosis (K. Kurasawa et al., *Arthritis Rheum* 43, 2455 (2000)) and psoriasis (C. Albanesi et al., *J Invest Dermatol* 115, 81 (2000), and B. Homey et al., *J Immunol* 164, 6621 (2000)). Although clearly produced by activated T cells, previous reports have not provided clear classification of IL-17 within the paradigm of Th1 and Th2 polarized cytokine profiles.

IL-23 is a heterodimeric cytokine, sharing a subunit, termed p40, with interleukin-12 (IL-12), that combines with a unique subunit, p19 (B. Oppmann et al., *Immunity* 13, 715 (2000)). IL-23 has been reported to promote the proliferation of T cells, in particular memory T cells (D. M. Frucht, *Sci STKE* 2002 Jan. 8; 2002 (114):PE1). Transgenic p19 mice have been recently described to display profound systemic inflammation and neutrophilia (M. T. Wiekowski et al., *J Immunol* 166, 7563 (2001)).

No correlation has so far been established between the expression and biological roles of the IL-17 and IL-23 cytokines.

SUMMARY OF THE INVENTION

In one aspect, the invention concerns a method for inhibiting interleukin-17 (IL-17) production by T cells comprising treating the T cells with an antagonist of interleukin-23 (IL-23).

In another aspect, the invention concerns a method for the treatment of an inflammatory disease characterized by elevated expression of interleukin 17 (IL-17) in a mammalian subject, comprising administering to the subject an effective amount of an antagonist of interleukin-23 (IL-23).

In yet another aspect, the invention concerns a method for identifying an anti-inflammatory agent comprising the steps of:
(a) incubating a culture of T cells with IL-23, in the presence and absence of a candidate molecule;
(b) monitoring the level of IL-17 in the culture; and
(c) identifying the candidate molecule as an anti-inflammatory agent if the level of IL-17 is lower in the presence than in the absence of such candidate molecule.

In a further aspect, the invention concerns a method for inducing IL-17 production in a mammalian subject comprising administering to said subject an IL-23 agonist.

In all aspects, the antagonist or agonist preferably is an anti-IL-23 or anti-IL-23 receptor antibody, including antibody fragments. The inflammatory disease preferably is a chronic inflammatory condition, such as, for example, rheumatoid arthritis (RA), graft versus host reaction that may lead to allograft rejection, multiple sclerosis (MS) or psoriasis. The induction of IL-17 production is typically useful in patients subjected to bacterial infection, such as, for example, infection *Mycobacterium tuberculosis*.

BRIEF DESCRIPTION OF THE DRAWINGS

FIG. 5: Effect of IL-12 on IL-17 production. (A) Mononuclear cells isolated from spleen cell cultures were incubated in the presence purified IL-23 (1 nM) and the indicated concentration of IL-12 for 5 days and then washed and re-stimulated with ConA for another 24 hours. IL-17 levels were measured in cell supernatant using ELISA kits. (B): Mononuclear cells isolated from spleen cell cultures from wild type or mice lacking IL-12Rβ2 (IL-12Rβ2$^{-/-}$ ko) were incubated in the presence or absence of purified IL-23 (1 nM) for 5 days and then washed and re-stimulated with ConA for another 24 hours. IL-17 and IFN-γ levels were measured in cell supernatant using ELISA kits.

FIG. 6: Targeting of the IL-23p19 locus. A: The native IL-23p19 locus (top), the targeting construct (middle), and the correctly targeted locus (bottom) are depicted to scale unless otherwise indicated by double slashes. Open boxes indicate coding exons, and hatched boxes represent exons encoding 5' and 3' untranslated regions of the resulting messenger RNA (mRNA). The four coding exons of the p19 gene are numbered. Boxes with arrows indicate the promoter regions for neomycin (neo) and thymidine kinase (tk) selection cassettes, and an open box labeled EGFP indicates the location of an enhanced green fluorescent protein reporter gene. Restriction sites used for cloning and analysis of the arms are labeled as follows: B, Bam HI; S, Sac II; E, Eco RI; Bg, Bgl II; X, Xho I. The location of an antisense primer used to amplify the short arm is indicated by the letter P and an arrow. The size of restriction fragments resulting from digestion with Bam HI and Eco RI are indicated in the wild type (WT) and the mutated (MUT) locus, and the locations of two probes used to detect these fragments by southern blot are shown by thick lines. B and C: Southern blot analysis of Bam HI digests probed with probe 1, and Eco RI digests probed with probe II, respectively. DNA was extracted from wild-type (WT) embryonic stem (ES) cells, from ES clone 1c5, and from a wild type, a heterozygous (HET), and a knockout (KO) mouse. The identity of the band is indicated at the left side of the blot, while its size is given on the right side.

FIG. 8: Humoral immune response in IL-23p19 mice. A-G: Ovalbumin (OVA) specific levels of IgG1 (A), IgG2a (B), IgG2b (C), IgG3 (D), IgE (E), and IgA (F) after one (1$^{st}$) and two (2$^{nd}$) immunizations with OVA. Filled circles, wild-type mice; open circles, and IL-23p19$^{-/-}$ mice, gray circles, and IL-12p40$^{-/-}$ mice. Arbitrary units were calculated as described in methods and materials. The average of each group is indicated by both a black horizontal bar and a numeric value at the bottom of the graph. Asterisks mark statistically significant P-values of less than 0.05.

DETAILED DESCRIPTION OF THE PREFERRED EMBODIMENT

A. Definitions

Figure 1:
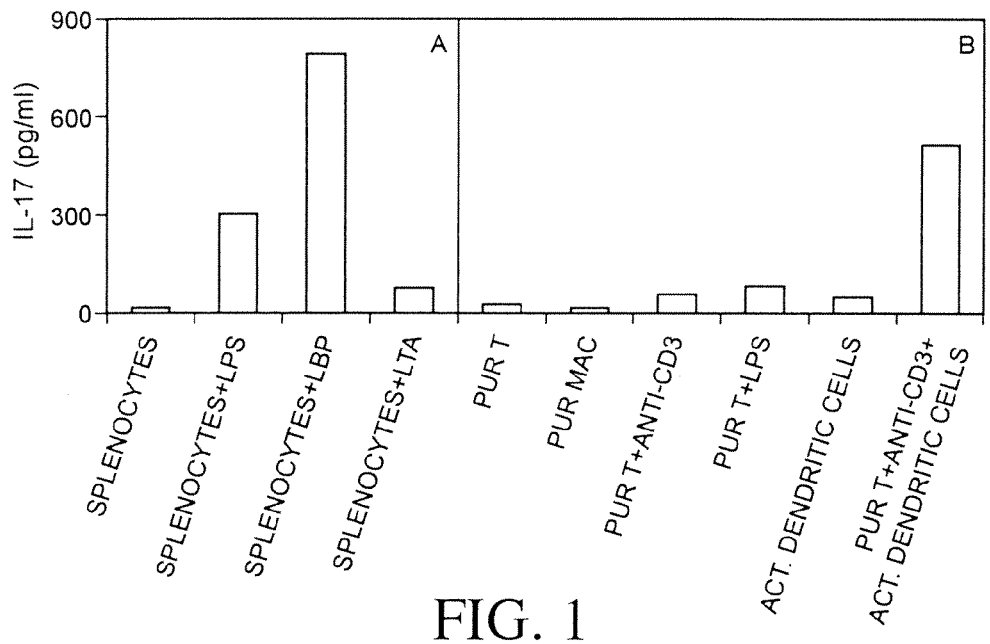
FIG. 1: IL-17 production in different cell types (A): Single cell suspensions of spleen were prepared from C57/BL-6 mice and mononuclear cells were isolated from suspended splenocytes by density gradient centrifugation. $2 \times 10^6$ cells/ml were cultured in the presence or absence of microbial lipopeptide LBP (100 ng/ml), LPS (100 ng/ml) or LTA (100 ng/ml) for 3 days, following which the cells were collected and analyzed for IL-17 using ELISA. (B): Purified T cells were obtained from murine splenocytes following positive selection of FACS sorted CD90 labeled cells. These cells were cultured ($1 \times 10^6$ cells/ml) in presence or absence of plate-bound anti-CD3 (5 μg/ml), or supernatant from activated dendritic cells (LPS-treated) for 3 days and culture supernatants collected and analyzed for IL-17 levels using ELISA kit. Dendritic cells were derived from macrophages (obtained as adherent population from splenocyte suspension), by treating macrophages with rmGM-CSF (2 ng/ml) and rmIL-4 (1000 U/ml) for 4 days, washing and re-activating using LPS (0.5 μg/ml). Representative results from 3 independent experiments are shown.

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). For purposes of the present invention, the following terms are defined below.

The term "antagonist" is used herein in the broadest sense. An IL-23 "antagonist" is a molecule, which partially or fully bocks, inhibits, neutralizes, prevents or interferes with a biological activity of IL-23, regardless of the underlying mechanism. For the purpose of the present invention, the biological activity preferably is the ability to induce IL-17 production in activated T cells. Antagonists of IL-23 can be identified, for example, based upon their ability to inhibit, block, or reverse IL-23 mediated IL-17 production in activated (e.g. memory) T cell populations. For example a culture of activated T cells can be incubated with IL-23, in the presence and absence of a test compound, and IL-17 level monitored in the cell culture supernatant, e.g. by ELISA. If the IL-17 level is lower in the presence of the test compound than in its absence, the test compound is an IL-23 antagonist. Alternatively, real-time RT-PCR can be used to monitor IL-17 mRNA expression in a tissue also expressing IL-23, before and after treatment with a test compound. Decrease in IL-17 mRNA level in the presence of the test compound indicates that the compound is an IL-23 antagonist. Examples of IL-23 antagonists include, without limitation, neutralizing antibodies against a subunit, e.g. a p40 subunit, of a native sequence IL-23 polypeptide, immunoadhesins comprising an IL-23 subunit fused to an immunoglobulin constant region sequence, small molecules, antisense oligonucleotides capable of inhibiting translation and/or transcription of a gene encoding a subunit of a native sequence IL-23 polypeptide, decoys, e.g. genetic decoys of the IL-23 gene, etc. Similarly, IL-23 antagonist include, without limitation, neutralizing antibodies against a subunit, e.g. an IL-12Rβ1 or IL-23R subunit, of a native IL-23 receptor, immunoadhesins comprising an IL-23 receptor subunit fused to an immunoglobulin constant region sequence, small molecules, antisense oligonucleotides capable of inhibiting translation and/or transcription of a gene encoding a subunit of a native sequence IL-23 receptor polypeptide, decoys, e.g. genetic decoys of an IL-23 receptor gene, etc.

The term "agonist" is used herein in the broadest sense. An IL-23 agonist is any molecule that mimics a biological activity mediated by a native sequence IL-23, regardless of the underlying mechanism. For the purpose of the present invention, the biological activity preferably is the ability to induce IL-17 production in activated T cells. Examples of IL-23 agonists include, without limitation, agonist antibodies against a subunit, e.g. an IL-12Rβ1 or IL-23R subunit, of a native IL-23 receptor, peptides and small organic molecules.

"Antisense oligodeoxynucleotides" or "antisense oligonucleotides" (which terms are used interchangeably) are defined as nucleic acid molecules that can inhibit the transcription and/or translation of target genes in a sequence-specific manner. The term "antisense" refers to the fact that the nucleic acid is complementary to the coding ("sense") genetic sequence of the target gene. Antisense oligonucleotides hybridize in an antiparallel orientation to nascent mRNA through Watson-Crick base-pairing. By binding the target mRNA template, antisense oligonucleotides block the successful translation of the encoded protein. The term specifically includes antisense agents called "ribozymes" that have been designed to induce catalytic cleavage of a target RNA by addition of a sequence that has natural self-splicing activity (Warzocha and Wotowiec, "Antisense strategy: biological utility and prospects in the treatment of hematological malignancies." *Leuk. Lymphoma* 24:267-281 [1997]).

The term "antibody" is used in the broadest sense and specifically covers monoclonal antibodies (including antagonist, e.g. neutralizing antibodies and agonist antibodies), polyclonal antibodies, multi-specific antibodies (e.g., bispecific antibodies), as well as antibody fragments. The monoclonal antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 [1984]). The monoclonal antibodies further include "humanized" antibodies or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature,* 321:522-525 (1986); and Reichmann et al., *Nature,* 332:323-329 (1988). The humanized antibody includes a PRIMATIZED® antibody wherein the antigen-binding region of the antibody is derived from an antibody produced by immunizing macaque monkeys with the antigen of interest.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10):1057-1062 (1995)); single-chain antibody molecules; and multispecific antibodies formed from antibody fragments.

As used herein, the term "inflammatory disease" or "inflammatory disorder" refers to pathological states resulting in inflammation, typically caused by neutrophil chemotaxis. Examples of such disorders include inflammatory skin diseases including psoriasis and atopic dermatitis; systemic scleroderma and sclerosis; responses associated with inflammatory bowel disease (IBD) (such as Crohn's disease and ulcerative colitis); ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms; cerebral edema secondary to stroke; cranial trauma, hypovolemic shock; asphyxia; adult respiratory distress syndrome; acute-lung injury; Behcet's Disease; dermatomyositis; polymyositis; multiple sclerosis (MS); dermatitis; meningitis; encephalitis; uveitis; osteoarthritis; lupus nephritis; autoimmune diseases such as rheumatoid arthritis (RA), Sjorgen's syndrome, vasculitis; diseases involving leukocyte diapedesis; central nervous system (CNS) inflammatory disorder, multiple organ injury syndrome secondary to septicaemia or trauma; alcoholic hepatitis; bacterial pneumonia; antigen-antibody complex mediated diseases including glomerulonephritis; sepsis; sarcoidosis; immunopathologic responses to tissue/organ transplantation; inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis; etc. The preferred indications include, without limitation, chronic inflammation, autoimmune diabetes, rheumatoid arthritis (RA), rheumatoid spondylitis, gouty arthritis and other arthritic conditions, multiple sclerosis (MS), asthma, systhemic lupus erythrematosus, adult respiratory distress syndrome, Behcet's disease, psoriasis, chronic pulmonary inflammatory disease, graft versus host reaction, Crohn's Disease, ulcerative colitis, inflammatory bowel disease (IBD), Alzheimer's disease, and pyresis, along with any disease or disorder that relates to inflammation and related disorders.

The terms "treat" or "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

"Chronic" administration refers to administration of the agent(s) in a continuous mode as opposed to an acute mode, so as to maintain the desired effect for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

A "subject" is a vertebrate, preferably a mammal, more preferably a human.

The term "mammal" is used herein to refer to any animal classified as a mammal, including, without limitation, humans, domestic and farm animals, and zoo, sports, or pet animals, such as sheep, dogs, horses, cats, cows, etc. Preferably, the mammal herein is human.

An "effective amount" is an amount sufficient to effect beneficial or desired therapeutic (including preventative) results. An effective amount can be administered in one or more administrations.

B. Modes of Carrying Out the Invention

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", 2" edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

As discussed before, the invention is based on the recognition that IL-23 induces IL-17 production in activated T cell, in particular memory cells, and that IL-23 antagonists are capable of inhibiting this process. Accordingly, IL-23 antagonists are promising drug candidates for the treatment of inflammatory conditions characterized by elevated levels of IL-17. Conversely, IL-23 agonists are useful to induce protective immune response to various infections, including Mycobacterial infections, such as, for example, *Mycobacterium tuberculosis* (*M. tuberculosis*) infection.

1. Screening Assays to Identify IL-23 Antagonists or Agonists

This invention includes screening assays to identify IL-23 antagonists, which find utility in the treatment of inflammatory conditions characterized by the presence of elevated levels of IL-17. The invention further includes screening assays to identify IL-23 agonists that find utility in stimulating a protective immune response to infections, such as infections by *Mycobacterium tuberculosis*.

Screening assays for antagonist drug candidates may be designed to identify compounds that bind or complex with IL-23 (including a subunit or other fragment thereof) or with an IL-23 receptor (including a subunit or other fragment thereof), or otherwise interfere with the interaction of IL-23 with other cellular proteins, thereby interfering with the production or functioning of IL-23. The screening assays provided herein include assays amenable to high-throughput screening of chemical libraries, making them particularly suitable for identifying small molecule drug candidates. Generally, binding assays and activity assays are provided.

The assays can be performed in a variety of formats, including, without limitation, protein-protein binding assays, biochemical screening assays, immunoassays, and cell-based assays, which are well characterized in the art.

All assays for antagonists and agonists are common in that they call for contacting the drug candidate with an IL-23 polypeptide, or and IL-23 receptor polypeptide, or a fragment of such polypeptides (specifically including IL-23 and IL-23 receptor subunits) under conditions and for a time sufficient to allow these two components to interact. For example, the human IL-23 p19 subunit is a 189 amino acid polypeptide, the sequence of which is available from the EMBL database under Accession Number AF301620 (NCBI 605580; Gen- Bank AF301620; Oppmann et al., supra). The sequence of subunit p40 of the IL-23 polypeptide is also known (also known as IL-12 p40 subunit; NCBI 161561). The sequence of IL-12Rβ1, to which IL-23 binds, is available under Accession Number NCBI 601604. The making of antibodies or small molecules binding to such polypeptides is well within the skill of the ordinary artisan.

In binding assays, the interaction is binding, and the complex formed can be isolated or detected in the reaction mixture. In a particular embodiment, either the IL-23 or IL-23 receptor polypeptide or the drug candidate is immobilized on a solid phase, e.g., on a microtiter plate, by covalent or non-covalent attachments. Non-covalent attachment generally is accomplished by coating the solid surface with a solution of the IL-23 or IL-23 receptor polypeptide and drying. Alternatively, an immobilized antibody, e.g., a monoclonal antibody, specific for the IL-23 polypeptide or the IL-23 receptor polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound is a polypeptide which interacts with but does not bind to IL-23 or the IL-23 receptor, its interaction with the respective polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (London), 340:245-246 (1989); Chien et al., *Proc. Natl. Acad. Sci. USA,* 88:9578-9582 (1991)) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of IL-23 and other intra- or extracellular components, in particular IL-17, can be tested as follows. Usually a reaction mixture is prepared containing IL-23 and the intra- or extracellular component (e.g. IL-17) under conditions and for a time allowing for the interaction of the two products. To test the ability of a candidate compound to inhibit the interaction of IL-23 and IL-17, the reaction is run in the absence and in the presence of the test compound. In addition, a placebo may be added to a third reaction mixture, to serve as positive control. Since IL-23 has been shown to induce IL-17 production, the ability of the test compound to inhibit the IL-23/IL-17 interaction can, for example, be tested by measuring the amount of IL-17 in the absence and presence of the test compound. If the IL-17 amount is lower in the absence of the candidate compound than in its presence, the candidate compound is an IL-23 antagonist by the definition of the present invention.

The IL-23 antagonists identified based upon their ability to inhibit the induction of IL-17 production by IL-23 are drug candidates for the treatment of inflammatory conditions characterized by the presence of elevated levels of IL-17.

The IL-23 agonists identified by upon their ability to promote the induction of IL-17 production by IL-23 are drug candidates for evoking or supporting a protective immune response to infections, such as infection by *Mycobacterium tuberculosis*, and, as a result, for the treatment of infectious diseases, such as tuberculosis.

It is emphasized that the screening assays specifically discussed herein are for illustration only. A variety of other assays, which can be selected depending on the type of the antagonist candidates screened (e.g. polypeptides, peptides, non-peptide small organic molecules, nucleic acid, etc.) are well know to those skilled in the art and are equally suitable for the purposes of the present invention.

2. Anti-IL-23 and Anti-IL-23 Receptor Antibodies

In a particular embodiment, the IL-23 antagonists or agonists are monoclonal antibodies to IL-23 (e.g. a subunit of IL-23), including antibody fragments. In another particular embodiment, the IL-23 antagonists and agonists include monoclonal antibodies to an IL-23 receptor (e.g. a subunit of an IL-23 receptor). IL-23, including its subunits, has been discussed hereinabove. The receptor for IL-23 is comprised of two subunits, IL-121431, and a more recently discovered subunit termed IL-23R (Parham et al., *J. Immunol.* 168:5699-5798 (2002)). Antibodies to either subunit are specifically within the scope of the invention. In case of antagonists, antibodies specifically binding the IL-23R subunit are particularly preferred, since they specifically block the biological activities mediated by IL-23.

Methods for making monoclonal antibodies are well known in the art. Thus, monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the IL-23 or IL-23 receptor polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against IL-23 or an IL-23 receptor. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies.

The anti-IL-23 and anti-IL-23 receptor antibodies of the invention may further be humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321: 522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Mono-* clonal Antibodies and Cancer Therapy, Alan R. Liss, p. 77 (1985) and Boerner et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Mendez et al. (Nature Genetics 15: 146-156 (1997)) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous $J_H$ segment as described above. The Xenomouse II harbors 1,020 kb of human heavy chain locus containing approximately 66 $V_H$ genes, complete $D_H$ and $J_H$ regions and three different constant regions (μ, δ and χ), and also harbors 800 kb of human κ locus containing $V_κ$ genes, $J_κ$ segments and $C_κ$ genes. The antibodies produced in these mice closely resemble that seen in humans in all respects, including gene rearrangement, assembly, and repertoire. The human antibodies are preferentially expressed over endogenous antibodies due to deletion in endogenous $J_H$ segment that prevents gene rearrangement in the murine locus.

Alternatively, the phage display technology (McCafferty et al., Nature 348, 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S, and Chiswell, David J., Current Opinion in Structural Biology 3, 564-571 (1993). Several sources of V-gene segments can be used for phage display. Clackson et al., Nature 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222, 581-597 (1991), or Griffith et al., EMBO J. 12, 725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technol. 10, 779-783 [1992]). In this method, the affinity of "primary" human antibodies obtained by phage display can be improved by sequentially replacing the heavy and light chain V region genes with repertoires of naturally occurring variants (repertoires) of V domain genes obtained from unimmunized donors. This techniques allows the production of antibodies and antibody fragments with affinities in the nM range. A strategy for making very large phage antibody repertoires has been described by Waterhouse et al., Nucl. Acids Res. 21, 2265-2266 (1993).

Various techniques have been developed for the production of antibody fragments. Traditionally, these fragments were derived via proteolytic digestion of intact antibodies (see, e.g., Morimoto et al., J. Biochem. Biophys. Methods 24:107-117 (1992) and Brennan et al., Science 229:81 (1985)). However, these fragments can now be produced directly by recombinant host cells. For example, Fab'-SH fragments can be directly recovered from E. coli and chemically coupled to form F(ab')$_2$ fragments (Carter et al., Bio/Technology 10:163-167 (1992)). In another embodiment, the F(ab')$_2$ is formed using the leucine zipper GCN4 to promote assembly of the F(ab')$_2$ molecule. According to another approach, Fv, Fab or F(ab')$_2$ fragments can be isolated directly from recombinant host cell culture. Other techniques for the production of antibody fragments will be apparent to the skilled practitioner.

Heteroconjugate antibodies, composed of two covalently joined antibodies, are also within the scope of the present invention. Such antibodies have, for example, been proposed to target immune system cells to unwanted cells (U.S. Pat. No. 4,676,980), and for treatment of HIV infection (PCT application publication Nos. WO 91/00360 and WO 92/200373). Heteroconjugate antibodies may be made using any convenient cross-linking methods, using well known, commercially available cross-linking agents.

For further information concerning the production of monoclonal antibodies see also Goding, J. W., Monoclonal Antibodies: Principles and Practice, 3rd Edition, Academic Press, Inc., London, San Diego, 1996; Liddell and Weeks: Antibody Technology: A Comprehensive Overview, Bios Scientific Publishers: Oxford, UK, 1995; Breitling and Dubel: Recombinant Antibodies, John Wiley & Sons, New York, 1999; and Phage Display: A Laboratory Manual, Barbas et al., editors, Cold Springs Harbor Laboratory, Cold Spring Harbor, 2001.

3. Target Diseases

IL-17 has been implicated in various inflammatory diseases, including rheumatoid arthritis (RA). One of the cardinal features of RA is erosion of periarticular bone. Osteoclasts play a key role in bone resorption but the mechanisms by which osteoclasts are formed from progenitor cells is not fully understood. Recently, Kotake, et al. (J. Clin. Invest. 103:1345 (1999)) reported that Interleukin 17 (IL-17) could induce the formation of osteoclast-like cells in cocultures of mouse hemopoietic cells and primary osteoblasts. This IL-17 induced osteoclastogenesis was shown to be inhibited by indomethacin, a selective inhibitor of cyclooxygenas-2 (COX-2). The synovial fluids from RA patients were found to contain significantly higher levels of IL-17 as compared to osteoarthritis (OA) patients. In addition, using immunostaining, IL-17-positive mononuclear cells were detected in the synovial tissues of RA patients and not in tissue from OA patients. These findings have been interpreted to indicate that IL-17 may contribute to bone erosion and joint damage in RA and may therefore, be a target for inhibition.

Behcet's disease patients have also been shown strinkingly elevated serum levels of IL-17 compared to healthy subjects. Hamzaoui et al., *Scand. J. Rheumatol.* 31(4):205-10 (2002).

Elevated levels of IL-17 have been found within asthmatic airways, and it has been suggested that IL-17 might amplify inflammatory responses through the release of other proinflammatory mediators, such as alpha-chemokines. Molet et al., *J. Allergy Clin. Immunol.* 108(3):430-8 (2001); and Wong et al., *Clin. Exp. Immunol.* 125(2):177-83 (2001).

Elevated levels of IL-17 have been reported for patients with systhemic lupus erythrematosus. Wong et al., *Lupus* 9(8):589-93 (2000).

IL-17 has been described to play a role in psoriasis. Homey et al., *J. Immunol.* 164(12):6621-32 (2000).

It has been reported that IL-17 mRNA is augmented in blood and CSF mononuclear cells in multipe sclerosis. Matusevicius et al., *Mult. Scler.* 5(2):101-4 (1999).

Based on these and numerous similar reports, IL-23 antagonists, which inhibit the ability of IL-23 to induce IL-17 production, and thereby lower IL-17 levels, are valuable candidates for the treatment of a variety of (chronic) inflammatory conditions and diseases. Examples of such conditions and diseases include, without limitation: chronic inflammation, autoimmune diabetes, rheumatoid arthritis (RA), rheumatoid spondylitis, gouty arthritis and other arthritic conditions, multiple sclerosis (MS), asthma, systhemic lupus erythrematosus, adult respiratory distress syndrome, Behcet's disease, psoriasis, chronic pulmonary inflammatory disease, graft versus host reaction, Crohn's Disease, ulcerative colitis, inflammatory bowel disease (IBD), Alzheimer's disease, and pyresis.

IL-17 is known to play an important role in the generation of a protective response to certain infectious diseases, such as tuberculosis by promoting IFN-γ production and thereby inducing a cell-mediated immune response. Accordingly, IL-23 agonists, including agonist antibodies, find utility in inducing a cell-mediated immune response to various infections, such as tuberculosis causes by *Mycobacterium tuberculosis*, and are promising drug candidates for treating this infectious disease which kills more than three million people worldwide every year.

4. Pharmaceutical Compositions

Antibodies specifically binding IL-23 or an IL-23 receptor, as well as other IL-23 antagonist or agonist molecules identified by the screening assays disclosed hereinbefore, can be administered for the treatment of various disorders, in particular inflammatory diseases or diseases benefiting from the induction of cell-mediated immune response, in the form of pharmaceutical compositions.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993).

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulation herein may also contain more than one active compound as necessary for the particular indication being treated, preferably those with complementary activities that do not adversely affect each other. Such molecules are suitably present in combination in amounts that are effective for the purpose intended, or may be formulated separately, and administered concurrently or consecutively, in any order.

For example, the IL-23 antagonists of the present invention may be administered in combination with anti-inflammatory agents and other active compounds currently in use for the treatment of the target diseases and conditions. Such compounds include corticosteroids; non-steroidal anti-inflammatory drugs (NSAIDs), such as aspirin, ibuprofen, and COX-2 inhibitors, e.g. Celebrex® and Vioxx®; disease-modifying anti-rheumatic drugs (DMARDs), such as methotrexate, leflunomide, sulfasalazine, azathioprine, cyclosporine, hydroxychloroquine, and D-penicillamine; and biological response modifiers (BRMs), such as TNF and IL-1 inhibitors.

The following examples are offered for illustrative purposes only, and are not intended to limit the scope of the present invention in any way.

All patent and literature references cited in the present specification are hereby incorporated by reference in their entirety.

EXAMPLE 1

Interleukin-23 (IL-23) Promotes a Distinct CD4 T cell Activation State Characterized by the Production of Interleukin-17 (IL-17)

Although clearly produced by activated T cells, previous reports have not provided clear classification of IL-17 within the paradigm of Th1 and Th2 polarized cytokine profiles. The purpose of the initial experiments described in this Example was to examine the possibility that IL-17 is expressed in response to signals distinct from those associated with the Th1 or Th2 response.

Experimental Procedures

Cell Culture—Single cell suspensions of spleen were prepared from C57/BL-6 mice, and mononuclear cells were isolated from suspended splenocytes by density gradient centrifugation. $2\times10^6$ cells/ml were cultured with IL-2 (100 units/ml) in the presence or absence of various stimuli (for times indicated in the figure legends), following which the cells were collected and analyzed for IL-17 using ELISA (R&D Systems, Minneapolis, Minn.). Dendritic cells were derived from macrophages (obtained as adherent population from splenocyte suspension) by treating mactophages with rGM-CSF (2 ng/ml) and rIL-4 (1000 unites/ml) for 4 days, washing and re-activating using LPS (0.5 µg/ml). Memory and naive T cells were isolated by staining mononuclear cells isolated from single cell suspension of murine splenocytes with CyC-CD4+PE-CD44 or CyC-CD4+PE-CD62L and sorting for CD4$^+$ cells that were either CD44$^{high}$/CD62L$^{low}$ for memory phenotype, or CD44$^{low}$/CD62$^{high}$ for naive phenotype.

In vitro Induction of T Cell Differentiation—CD4$^+$ cells were purified from spleen of wild type C57/BL6 mice using anti-CD4 magnetic beads (Miltenyi Biotech). Purified T cells ($2\times10^6$ cells/ml) were activated for 3 days by plating on plates coated with 5 µg/ml anti-CD3 and 1 g/ml anti-CD28 antibodies. The cultures were supplemented with IL-2 and treated with IL-12 (20 mM)+anti-IL4 (0.5 µg/ml) (for Th1 differentiation), or IL-23 (10 nM) (for IL-17 production). Following initial activation, the cell cultures were washed extensively and re-stimulated with anti-CD3 (1 µg/ml) for another 24 h, following which the cell supernatants were analyzed for various secreted cytokines using ELISA.

IL-12p40 Antibody Inhibition of IL-17 Induction—Anti-IL-12 antibody (R&D Systems, cat. no. AF-419-NA) or an unrelated control antibody (anti-FGF-8b (R&D Systems, cat. no. AF-423-NA) were pre-incubated with IL-23 (100 ng/ml) or conditioned media of LPS-stimulated dendritic cells (10% v/v) for 1 h at 37° C. and then incubated for another 5-6 days with mononuclear cells isolated from mouse spleen ($2\times10^6$ cells/ml). Supernatants were collected and levels of IL-17 measured using ELISA.

Purification of IL-23-Murine IL-23-IL-23 component was produced by co-expression of carboxyl-terminal His-tagged p19 and FLAG0tagged p40 in human embryonic kidney cells (293 cells), and secreted protein was purified by nickel affinity resin. Endotoxin levels were undetectable at less than 0.2 endotoxin units per µg.

Results

First, the ability of various microbial products to stimulate the production of IL-17 was examined. Increased IL-17 has recently been observed by Infante-Duarte et. al., *J Immunol* 165, 6107 (2000), in response to microbial lipopeptides from a Lyme disease causing spirochete, *B. burgdorferi*. Spleen cell cultures in the presence of various microbial peptides including LPS (gram-negative bacteria), LTA (gram positive bacteria) or LBP (bacterial lipopeptide) resulted in the production of IL-17 (FIG. 1). Neither purified T cells alone, nor purified macrophages themselves produced IL-17. Purified T cells, upon receptor cross-linking using plate-bound anti-CD3 and treatment with supernatants from activated macrophages/dendritic cells produced increased IL-17, indicating the presence of an unidentified factor(s) released by these cells that acts on T cells to promote IL-17 production.

In profiling the expression of candidate molecules that might be responsible for this IL-17 promoting activity, a 100-1000 fold increased mRNA expression of the IL-23 (B. Oppmann et al., *Immunity* 13, 715 (2000)) components p19 and p40 was observed in activated dendritic cells using real-time RT-PCR (not shown), hence, the effect of IL-23 was examined.

Murine IL-23 component was produced by co-expression of carboxyl terminal His-tagged p19 and Flag-tagged p40 in human embryonic kidney cells (293 cells) and secreted protein was purified by nickel affinity resin. Endotoxin levels were undetectable at less than 0.2 EU per µg. Spleen cell cultures were incubated in presence of IL-2 (100 U/ml) and ConA (2.5 µg/ml) under Th1-inducing conditions (IL-12+ anti-IL-4), Th2-inducing conditions (IL-4+ anti-IFN-γ), or purified IL-23 (100 ng/ml) for 3-4 days, following which, the cultures were washed and re-stimulated with ConA for another 24 hours. Levels of various cytokines were measured using ELISA. The levels less than the lowest dilution of the standard curve range of ELISA kit were recorded as 'not detectable (N.D.)'. The results below are representative of three experiments performed independently.

Spleen cells, cultured under IL-12-stimulated Th1-inducing conditions resulted in marginal IL-17 production, whereas under Th2-inducing conditions there was no increased production of IL-17 over controls. The results are shown in the following Table 1.

TABLE 1

|  | Control | IL-12 | IL-4 | IL-23 |
| --- | --- | --- | --- | --- |
| IL-17 | N.D | 58 ± 82 | 64 ± 91 | 1191 ± 569 |
| IL-4 | 50 ± 26 | 396 ± 17 | 3259 ± 118 | 101 ± 100 |
| IFN-γ | 341 ± 0 | 2757 ± 1016 | 489 ± 502 | 580 ± 813 |
| GM-CSF | N.D. | 46 ± 13 | 365 ± 516 | 882 ± 169 |
| TNF-α | N.D | 174 ± 40 | 214 ± 314 | 205 ± 85 |

Figure 2A:
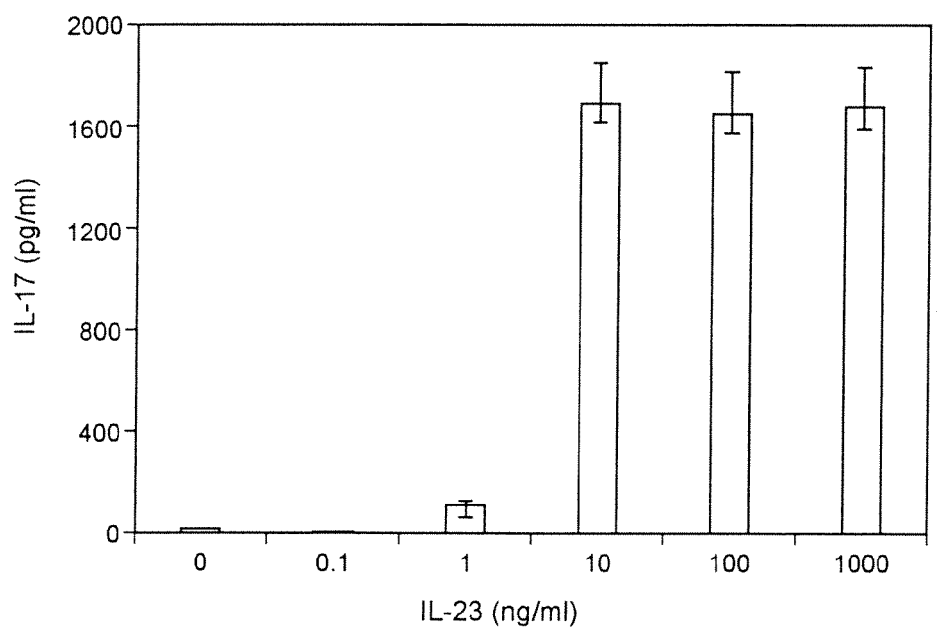
FIG. 2: IL-23 stimulates production of IL-17 A. Mononuclear cells isolated from splenocytes were cultured ($2 \times 10^6$ cells/ml) with 100 U/ml recombinant IL-2 and were incubated in presence or absence of various concentrations of IL-23 (0.1-1000 ng/ml) for 6 days. Levels of IL-17 accumulated in culture supernatants were measured using ELISA. B. Changes in mRNA levels for IL-17 in response to IL-23 treatment were measured by quantitative RT-PCR. Plotted is the relative change in Ct (cycle threshold) of the PCR reaction. Data for each sample is normalized to the glyceraldehyde-3-phosphate dehydrogenase mRNA level present in each sample and then normalized again between samples to the level of IL-17 mRNA present in the time zero unstimulated conditions. As each Ct corresponds to a PCR cycle, one Ct is approximately equal to a 2-fold change in mRNA abundance. The approximate mRNA fold difference for 5 Ct and 10 Ct changes are indicated in parenthesis. The experiment was performed with splenocytes from 4 mice, and the individual data points are represented with x and the average Ct change is indicated by bar columns. C. Changes in mRNA levels of the IL-17 family member IL-17F in response to IL-23 treatment were measured by quantitative RT-PCR as in the legend to FIG. 2B.
Figure 2B:
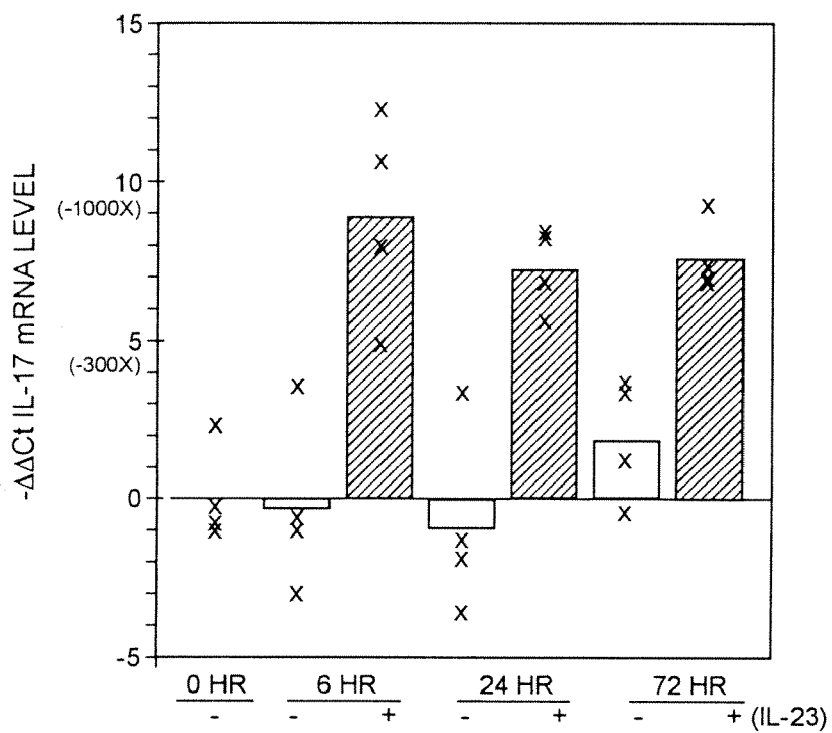
Figure 2C:
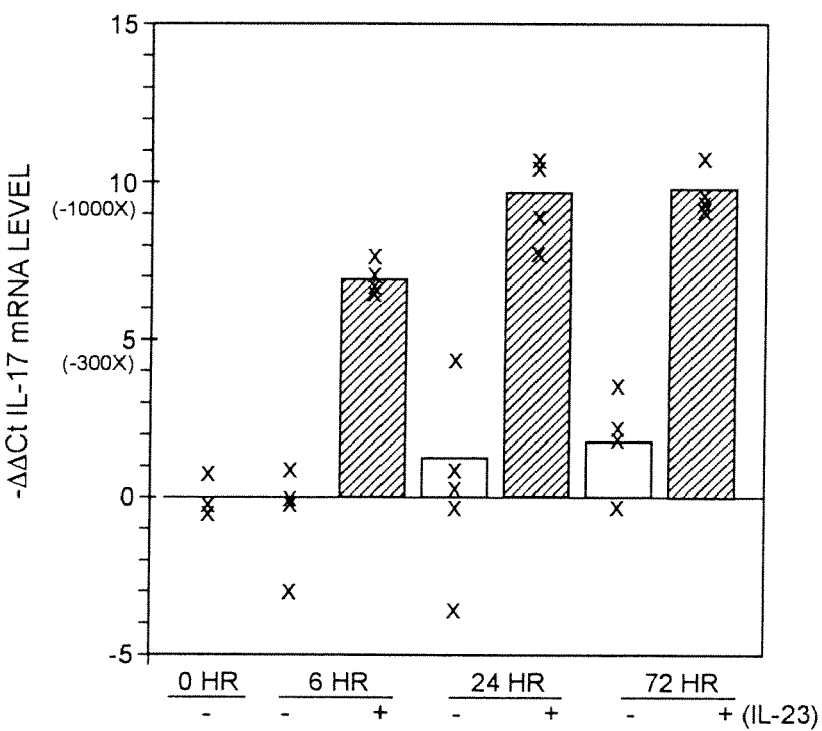

Presence of IL-23 in cultures resulted in high level IL-17 production, in a dose-dependent manner (FIG. 2). IL-23 also resulted in higher levels of GM-CSF than observed under Th1-inducing conditions. In contrast, IFN-γ levels were significantly lower than those obtained under Th1-inducing conditions. TNF-α levels were similar to Th1 conditions. IL-12p40 alone did not result in any IL-17 production (data not shown). IL-23 promoted elevated levels of IL-17 mRNA (FIG. 2B). IL-17 mRNA levels were increased several hundred-fold within 6 h of IL-23 exposure and remained elevated in the continued presence of IL-23. This effect was no inhibited by the presence of an antibody against IL-17, suggesting that the IL-17 itself was not contributing to this process (not shown). In addition, mRNA for IL-17F, a recently identified IL-17 family member, was also found to be upregulated in response to IL-23 (FIG. 2C).

Figure 3:
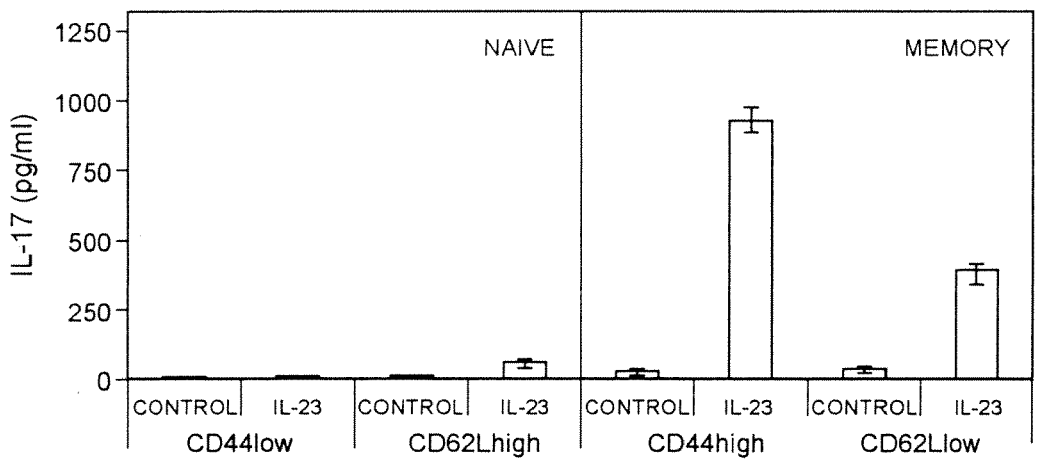
FIG. 3: IL-23 acts on memory T cells to induce IL-17 production Mononuclear cells isolated from single cell suspension of murine splenocytes were stained with (a) CyC-CD4+PE-CD44 or (b) CyC-CD4+PE-CD62L and sorted for CD4$^+$ cells that were either CD44$^{high}$/CD62L$^{low}$ for memory phenotype or CD44$^{low}$/CD62$^{high}$ for naïve phenotype. The sorted cells were cultured with 100 U/ML recombinant IL-2 in the presence or absence of IL-23 (or its boiled prep as a control), plate bound anti-CD3 (5 µg/ml) and anti-CD28 (1 µg/ml) for 5 days, washed, and re-stimulated with anti-CD3 antibody for another 24 hours. Supernatants were collected and IL-17 levels were measured using ELISA.

IL-23 has been reported to promote the proliferation of memory but not naïve T cells (D. M. Frucht, supra. Therefore, the effect of IL-23 on IL-17 production from naïve versus memory T cell populations was examined. Purified CD4$^+$ T cells were isolated from splenocytes by fluorescence activated cell sorting (FACS). The memory cell population was selected as CD4$^+$CD44$^{high}$ (R. C. Budd et al., *J Immunol* 138, 3120 (1987)), or CD4$^+$CD62L$^{low}$ (T. M. Jung, W. M. Gallatin, I. L. Weissman, M. O. Dailey, *J Immunol* 141, 4110 (1988)), and naïve cell population was selected as CD4$^+$CD44$^{low}$ or CD4$^+$CD62L$^{high}$. As seen in FIG. 3, IL-23 stimulated IL-17 production only in memory cell population (CD44$^{high}$ and CD62L$^{low}$) and not in naïve cells (CD44$^{low}$ or CD62L$^{high}$).

Figure 4A:
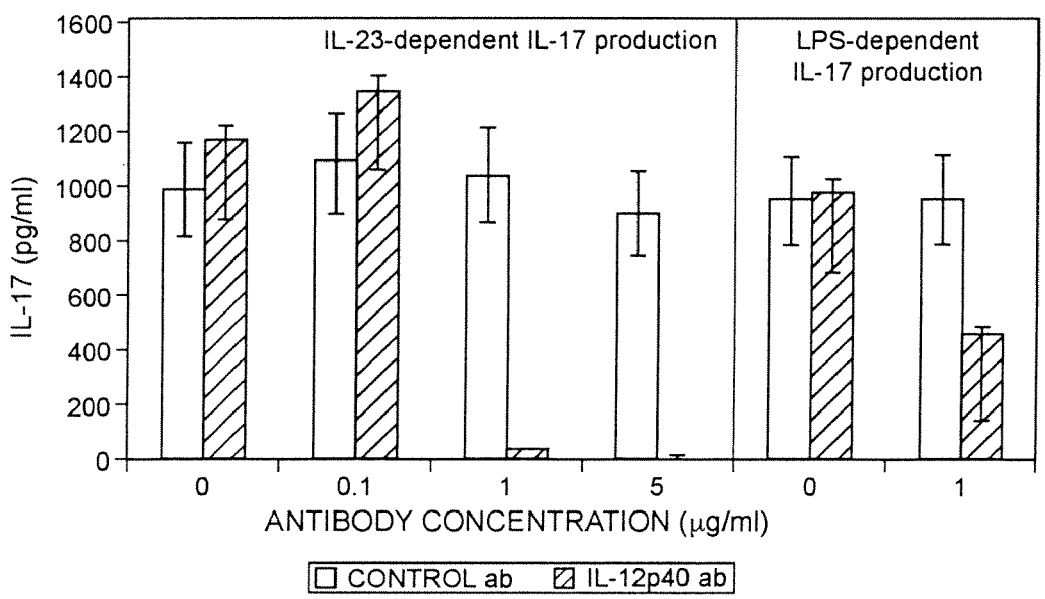
FIG. 4: IL12p40 antibody blocks IL-23-dependent IL-17 production: (A) Increasing concentrations of p40 antibody or an unrelated isotype-matched control antibody were pre-incubated with IL-23 (100 ng/ml) for 1 hr. at 37° C. and then incubated for another 5-6 days with mononuclear cells isolated from mouse spleen ($2\times10^6$ cells/ml) in presence of recombinant IL-2. Supernatant were harvested and levels of IL-17 measured using ELISA (left panel). Optimum concentrations of IL-12p40 antibody or an unrelated isotype-matched control antibody were pre-incubated with conditioned media of LPS-stimulated dendritic cells (10% v/v) for 1 hr. at 37° C. and then incubated for another 5 days with mononuclear cells isolated from mouse spleen ($2\times10^6$ cells/ml) in presence of recombinant IL-2. Supernatant were harvested and levels of IL-17 measured using ELISA (right panel). (B) Mononuclear cells isolated from splenocytes of wild type mice (C57/BL6) or mice lacking one of the components of IL-12, i.e. IL12a$^{-/-}$ (p35 knockout) or IL12b$^{-/-}$ (p40 knockout) were cultured in the presence of ConA for 3 days and IL-17 levels measured in supernatants using ELISA.

The IL-23-mediated IL-17 production was completely blocked in the presence of a neutralizing IL-12 antibody that interacts with the p40 subunit shared with IL-23 (FIG. 4A, left panel). This effect was not due to ligation of Fc receptors on antigen presenting cells as there was no change in IL-17 production in the presence of unrelated antibody. This antibody also inhibited >50 percent the induction of IL-17 production observed in response to conditioned media from LPS stimulated dendritic cells (FIG. 4A, right panel). A marked reduction, but not abrogation, of IL-17 production was seen in response to ConA stimulation from spleen cell cultures of mice lacking IL-12p40 component (strain: B6.129S1-IL12b$^{tm1Jm}$) as compared to wild type mice or mice lacking IL-12p35 component (strain: B6.129S1-IL12a$^{tm1Jm}$) (FIG. 4B).

In order to examine the role of IL-12 in IL-17 production, increasing amounts (0.001-1 nM) of murine IL-12 were added to IL-23 (1 nM) containing cultures. As seen in FIG. 5A, IL-12 decreased IL-17 levels in a dose dependent manner.

Additionally, splenocytes from mice lacking IL-12 receptor beta chain 2 (IL-12Rβ2) (Wu et al., *J Immunol* 165, 6221 (2000)), the specific receptor component of IL-12 (A. O. Chua, V. L. Wilkinson, D. H. Presky, U. Gubler, *J Immunol* 155, 4286 (1995)), were treated with purified IL-23. Splenocytes from IL-12Rβ2$^{-/-}$ mice responded to IL-23 stimulus by increasing IL-17 production over the un-stimulated control (FIG. 5B) without affecting IFN-γ levels. Surprisingly, the background levels of IL-17 in these mice were more than 10-fold as compared to wild-type mice, suggesting a possible negative regulation by IL-12 of IL-23-induced IL-17 production. However, in contrast to IL-12Rβ2 knockout mice, we did not observe increased IL-17 in spleen cultures from IL-12p35 knockout mice. The reasons for this difference are not known, but could relate to alteration in IL-12p40 function in the absence of p35, or differences in genetic background or pathogen exposure.

Discussion

Taken together, these data suggest a role for IL-23 in the promotion of a distinct T cell activation state that expresses IL-17 as an effector cytokine. The Th1 and Th2 paradigms have been described as promoting cell mediated versus humoral immune responses. These responses provide important defense for intracellular and extracellular pathogens respectively, and defects in either of these responses are associated with increased susceptibility to specific pathogens. In contrast, IL-23 may serve to promote an adaptive immune response to pathogens that is characterized by a heavy reliance on cells thought to function primarily as mediators of the innate immune response. IL-17, as a principle effector cytokine of this response, is able to promote the more rapid recruitment of monocytes and neutrophils through induced chemokine production. In addition, the high level GM-CSF production observed in response to IL-23 supports the production of additional myeloid cells. This is further augmented by G-CSF production from local IL-17-stimulated stromal cells. The character of this adaptive response is, however, not an exclusive reliance on phagocytic cells of the myeloid lineage response as IL-17 is known to promote the induction of ICAM by IL-17 thereby providing important co-stimulation of further T cells responses.

Recently, several studies have pointed out significant differences between mice deficient in p35 and mice deficient in p40 (Decken et al., *Infect Immun.* 66:4994-5000 (2002); Cooper et al., *J. Immunol.* 168:1322-1327 (2002); Elkins et al., *Infection & Immunity* 70:1936-1948; Holscher et al., *J. Immunol.* 167:6957-6966 (2001)). These studies share the observation that loss of p40 is generally more deleterious than loss of p35 in the immune-mediated clearance of a variety of model organisms.

The association of IL-17 expression with a number of serious inflammatory diseases suggests that IL-23 antagonists may be promising drug candidates in the treatment of such diseases.

EXAMPLE 2

Interleukin-23 (IL-23) Deficient Mice

To further investigate the relationship between IL-23 and IL-17 in vivo, the phenotype of IL-23 deficient mice was compared to that of IL-17 deficient animals.

Experimental Procedures

Mice: All mice were housed under specific pathogen free conditions. IL-12p40$^{-/-}$ mice were obtained from the Jackson laboratory (Bar Harbor, Mass.), and C57BL/6 were obtained from Charles River laboratories (San Diego, Calif.).

Reagents: Unless otherwise indicated, reagents were purchased from the following suppliers: Antibodies and ELISA reagents were obtained from B D Phammingen (San Diego, Calif.), cytokines from R&D systems (Minneapolis, Minn.), TNP-coupled antigens from Biosearch Technologies (Novato, Calif.) and tissue culture reagents from Invitrogen (Carlsbad, Calif.).

Generation of IL23p19 deficient mice. Genomic DNA encompassing the murine IL23p19 locus was isolated from clone 198a3 of a genomic BAC library by Genome Systems (Incyte Genomics, Palo Alto, Calif.). A targeting vector designed to replace the entire IL23p19 coding region with an EGFP reporter gene was constructed from the following DNA fragments using standard molecular cloning techniques: a thymidine kinase selection cassette; a 5' homology arm of 5403 base pairs defined by endogenous SacII and BglII sites on the distal and proximal ends, respectively; an EGFP expression cassette excised from pEGFP-1 (BD Clontech, Palo Alto, Calif.) using BamHI (5'-end) and AflIII (3'-end); a PGK-neo resistance cassette; and a 1203 by short arm defined by an endogenous XhoI site at the proximal end and the primer 5'-GCTTGGTGGCCCACCTATGAT-3' (SEQ ID NO: 1) at the distal end (FIG. 6A). This construct was electroporated into 129/SvEv embryonic stem (ES) cells (Huang et al., *Science* 259:1742 (1993)) and homologous recombination occurred in 9 out of 600 clones following selection with G418 and Gancyclovir. To verify correct targeting of the locus, genomic DNA from ES cells and animals was analyzed by southern blot. Digestion with BamHI followed by hybridization of membranes with probe 1 (a 831 by genomic DNA fragment obtained by PCR with oligos 5'-AGACCCT-CAAAGTTCATGAC-3' (sense) (SEQ ID NO: 2) and 5'-CT-GACGGCGCTTTCTCTACC-3' (antisense) (SEQ ID NO: 3)) yielded a 7027 by fragment for the wild-type allele and an 11788 by fragment for the correctly targeted mutant allele. Similarly, digestion of genomic DNA with EcoRI followed by hybridization of membranes with probe 2 (a 390 by genomic DNA fragment obtained by PCR with oligos 5'-TTTTGCCAGTGGGATACACC-3' (sense) (SEQ ID NO: 4) and 5'-AACTGCTGGGGCTGTTACAC-3' (antisense) (SEQ ID NO: 5)) yielded a 9197 by fragment for the wild-type allele and an 6211 by fragment for the correctly targeted mutant allele. Two ES cell clones (1c5 and 3h6) were injected into blastocysts, and chimeric animals that transmitted the mutant allele in their germline were obtained. For routine genotyping, we used a PCR-based method with a common antisense primer (5'-GCCTGGGCTCACTTTTTCTG-3') (SEQ ID NO: 6), and wild-type specific (5'-GCGT-GAAGGGCAAGGACACC-3') (SEQ ID NO: 7) and knock-out-specific (5'-AGGGGGAGGATTGGGAAGAC-3' (SEQ ID NO: 8)) sense primers. This primer-triplet amplifies a 210 by fragment for the wild-type allele and a 289 by fragment for the mutant allele. PCR was carried out in a Robocycler (Stratagene, La Jolla, Calif.), using the following conditions: 1 cycle of 94° C., 60"; 35 cycles of 94° C., 30", 58° C., 30", 72° C., 60"; 1 cycle of 72° C. 7".

FACS analysis of blood cell subsets: Spleens, thymi, and lymph nodes were isolated from 6-8 week old mice, and single cell suspensions were prepared by standard methods. Peripheral blood was obtained by cardiac puncture and treated with EDTA to prevent coagulation, and erythrocytes were lysed using ACK lysing buffer (Biosource, Camarillo, Calif.). All cells were incubated for 30 minutes on ice in Hanks balanced salt solution (HBSS) supplemented with 2% heat inactivated bovine calf serum. Cells were then stained in the same buffer with 1 µg per million cells of various antibodies coupled to phycoerythrin, biotin or Cychrome™. Where biotinylated antibodies were used, streptavidin-coupled PE-TR conjugate (Caltag, Burlingame, Calif.) was used for detection. After two washes with the same buffer, fluorescence was detected using an Epics-XL flow cytometry system (Beckman Coulter Inc., Fullerton, Calif.).

Stimulation of allotypic T-cells: CD4 and CD62L double positive T-cells were isolated from the spleens of 6-8 week old balb/c mice by a two-step isolation protocol. First, T-cells were depleted of other cell types by a negative magnetic selection (Miltenyi, Auburn, Calif.). These cells were then labeled with antibodies against CD4 and CD62L and sorted by FACS on a MoFlo sorter (DakoCytomation, Fort Collins, Colo.). Dendritic cells from wild type or IL-23p19$^{-/-}$ mice, both in the C57BL/6 background, were also isolated by a two-step protocol. CD11c positive splenocytes were positive selected by magnetic separation (Miltenyi, Auburn, Calif.) prior to labeling with antibodies against CD11c, MHC class II, and CD8. CD11c$^+$/MHC-II$^+$/CD8$^-$ cells were then sorted by FACS, again using a MoFlo sorter. All populations used in the experiment were at least 98% pure. To elicit allostimulatory responses, $10^4$ dendritic cells and $10^5$ T-cells were incubated in a total of 200 µl of IMDM supplemented with penicillin-streptomycin and 10% heat inactivated bovine calf serum (Hyclone, Logan, Utah) in duplicates. In some cases, 100 ng/ml bacterial lipopeptides was added to stimulate cytokine production by dendritic cells. After 5 days of incubation, 120 µl of supernatant were removed for cytokine measurement by ELISA, and replaced with fresh medium containing 1 µCi $^3$H-thymidine per well. Thymidine incorporation was determined 16 hours later using a Top Count liquid scintillation counter according to the manufacturers instructions (Packard Instruments, Meriden, Conn.).

In vivo T-cell differentiation: Four male and four female mice per group were immunized into the left hind footpad with 75 µg of keyhole limpet hemocyanin (KLH) (Sigma, St. Louis, Mo.) in 30 µl of a 1:1 emulsion of CFA (BD Biosciences, San Diego, Calif.) and PBS. Draining inguinal and popliteal lymph nodes were harvested 5 days later and restimulated in IMDM supplemented with penicillin-streptomycin, 10% heat inactivated bovine calf serum (Hyclone, Logan, Utah), and 25 µg/ml KLH. For proliferation assay, 5*$10^5$ cells were seeded in 200 µl in triplicates in 96 well plates and allowed to proliferate for 112 hours with addition of 1 µCi $^3$H-thymidine per well during the last 18 hours of the incubation period. Thymidine incorporation was determined using a Top Count liquid scintillation counter according to the manufacturers instructions (Packard Instruments, Meriden, Conn.). For cytokine secretion, 2.5*$10^6$ cells were incubated in 1 ml in 48 well plates, and supernatants were harvested after 72 hours. Cytokine secretion was determined by ELISA. The data presented is one representative out of three total experiments.

Delayed type hypersensitivity responses: 6 mice per group were subcutaneously injected with 200 µg of methylated bovine serum albumin (mBSA) (Sigma, St. Louis, Mo.) at three sites in the abdomen in a combined total of 200 µl of a 1:1 emulsion of CFA (BD Biosciences, San Diego, Calif.) and PBS. On day 8 following immunization, the mice were challenged by injection of 20 µl of 5 mg/ml mBSA in PBS into one rear footpad, while the other rear footpad received 20 µl of PBS. Measurements of footpad swelling were taken at 18, 42, 66 hours after challenge, using a series 7 spring-loaded caliper (Mitutoyo, City of Industry, Calif.). The magnitude of the DTH responses was determined from differences in footpad thickness between the antigen- and PBS-injected footpads.

T-dependent humoral responses and immunoglobulin analysis: For the measurement of total immunoglobulin levels, serum was obtained from 8 male and 8 female, 6-9 week old, unimmunized mice of either genotype. Total immunoglobulin isotype levels were measured by Luminex bead assay (Upstate, Lake Placid, N.Y.). To assess the OVA specific humoral immune response, groups of 7 mice per genotype (4 males and 3 females) were immunized with OVA in CFA on day 0 and received booster immunizations of the same antigen in incomplete Freund's adjuvant (IFA) (Sigma, St. Louis, Mo.) on days 21 and 42. For serum analysis, blood was obtained by retro-orbital bleeding before immunization and on days 14, 28, and 49 after immunization. OVA specific immunoglobulin isotypes were detected by ELISA, using OVA as a capture agent and isotype specific secondary antibodies for detection. In order to be in the linear range of the ELISA, serum samples were diluted as follows: 1:3125000 for IgG1, 1:25000 for IgG2a, 1:625000 for IgG2b, and 1:1000 for IgG3, IgM, IgA and IgE. A dilution series of a serum obtained from an OVA-immunized mouse from a previous experiment was used as a standard, since purified, OVA specific isotypes are not commercially available. Results are expressed as arbitrary units, where the average of the wild-type group in the last bleed was set as 100. To assess the contribution of memory T-cells to the humoral response, groups of 5-6 mice of either genotype were immunized with OVA in CFA on day 0 and received a booster immunization of TNP$_{11}$-OVA in IFA on day 21. For serum analysis, blood was obtained by retro-orbital bleeding before immunization and on days 14 and 28 after immunization. TNP specific immunoglobulin isotypes were detected by ELISA, using TNP$_{28}$-BSA as a capture agent and isotype specific secondary antibodies for detection. For TNP-specific IgG1, a commercially available standard was used. For TNP-specific IgG2a, a dilution series of a serum obtained from a TNP immunized mouse from a previous experiment was used, and results were calculated as described above. The sample dilutions were 1:31250 for IgG1 and 1:1250 for IgG2a.

T-independent humoral responses: Groups of 6 mice per genotype were immunized intraperitoneally with 50 µg TNP$_1$-LPS or 100 µg TNP$_{20}$-AECM-Ficoll in PBS. Serum was harvested 10 days later, and TNP-specific IgM was analyzed by ELISA, using TNP$_{28}$-BSA as a capture agent and an IgM specific secondary antibody for detection. A TNP specific IgM antibody was used as a standard for the ELISA. The sample dilutions were 1:1280 for Ficoll and 1:5120 for LPS.

Results

Deletion of the IL-23p19 gene. To determine the non-redundant in vivo effects of IL-23, mice were generated that are deficient in IL-23 but competent to produce IL-12. A targeting vector was constructed in which the entire coding region of p19, consisting of 4 exons, is replaced by an enhanced GFP (eGFP) reporter gene, and a neomycin resistance cassette (FIG. 6). Germline transmission was obtained from two correctly targeted ES cell clones, 1c5 and 3h6, and the mutation was backcrossed into the C57BL/6 background using speed congenics with 3 markers per chromosome. Based on this analysis, only those mice were selected in which the genetic contamination from the 129 background was less than 5% for experiments. The pattern of eGFP expression was comparable to that of endogenous p19 mRNA (data not shown).

IL-23p19$^{-/-}$ mice have no overt phenotype. As expected from the phenotype of IL-23/IL-12 double deficient IL-12p40$^{-/-}$ mice, IL-23p19$^{-/-}$ animals did not display any overt phenotype and were born at mendelian frequencies. No abnormalities in organs were found upon histopathological examination, and further analysis of clinical chemistry and hematology parameters did not reveal differences between wild type and knockout animals. Furthermore, IL-23p19$^{-/-}$ mice were normal in size and weight, and both sexes were fully fertile. Flow cytometric analysis of thymocytes, splenocytes, and peripheral blood leukocytes with various cell surface markers did not indicate any major differences between wild-type and IL23p19$^{-/-}$ animals (Table 2). Because IL-23 is known to act on memory T-cells, we the ratio of memory (CD44$^{high}$CD62L$^-$) versus naïve (CD62L$^+$) cells of each subset was determined, but no difference was found between wild-type and IL-23p19$^{-/-}$ mice. In the entire analysis, the only noticeable difference between the two genotypes consists in a slight skewing of the dendritic cell subpopulations towards a CD8$^+$ phenotype. While the effect was minor, it reached statistical significance due to the tightness of the data, and could be compatible with recent observations that IL-23 has effects on antigen presenting cells. In summary, IL-23 does not appear to be required for normal development, and the introduction of an eGFP cassette does not have a toxic effect on any cell type tested.

TABLE 2

|  | wild-type | knockout | P (diff.) |
|---|---|---|---|
| Thymus |  |  |  |
| CD4+ | 5.7 +/− 0.5 | 5.5 +/− 0.0 | 0.504 |
| CD8+ | 3.3 +/− 0.1 | 3.1 +/− 0.3 | 0.397 |
| DN | 25.0 +/− 4.2 | 17.0 +/− 8.0 | 0.202 |
| DP | 65.9 +/− 3.7 | 74.3 +/− 8.0 | 0.174 |
| Spleen |  |  |  |
| CD4+ | 24.3 +/− 0.8 | 22.5 +/− 2.7 | 0.342 |
| % naïve | 69.0 +/− 1.3 | 67.5 +/− 2.1 | 0.090 |
| % memory | 29.1 +/− 1.2 | 31.0 +/− 1.9 | 0.029 |
| CD8+ | 15.2 +/− 1.2 | 12.3 +/− 2.0 | 0.101 |
| % naïve | 64.1 +/− 5.4 | 67.0 +/− 2.8 | 0.199 |
| % memory | 18.1 +/− 1.8 | 18.3 +/− 1.4 | 0.084 |
| I-A(b)+/CD11c+ | 2.0 +/− 0.2 | 2.2 +/− 0.2 | 0.041 |
| % CD8+ | 12.8 +/− 0.9 | 16.3 +/− 1.7 | 0.000 |
| % CD8− | 87.2 +/− 0.9 | 83.6 +/− 1.8 | 0.000 |
| CD19+ | 52.4 +/− 2.0 | 55.2 +/− 6.5 | 0.512 |
| B220+ | 52.0 +/− 2.0 | 55.5 +/− 5.3 | 0.360 |
| NK1.1+ | 3.2 +/− 0.1 | 2.8 +/− 0.1 | 0.055 |
| Peripheral blood |  |  |  |
| CD3+ | 47.9 +/− 2.6 | 44.9 +/− 3.6 | 0.053 |
| CD4+ | 28.2 +/− 2.3 | 26.9 +/− 2.5 | 0.270 |
| CD8+ | 16.5 +/− 0.8 | 15.6 +/− 1.7 | 0.150 |
| CD19+ | 43.2 +/− 3.2 | 45.2 +/− 3.6 | 0.215 |
| B220+ | 44.9 +/− 3.5 | 46.4 +/− 4.8 | 0.466 |
| DX5+ | 9.9 +/− 3.0 | 9.7 +/− 5.0 | 0.929 |
| CD16+ | 8.0 +/− 0.9 | 8.6 +/− 1.5 | 0.302 |
| I-A(b)+ | 44.0 +/− 1.9 | 45.4 +/− 4.9 | 0.428 |

Figure 7:
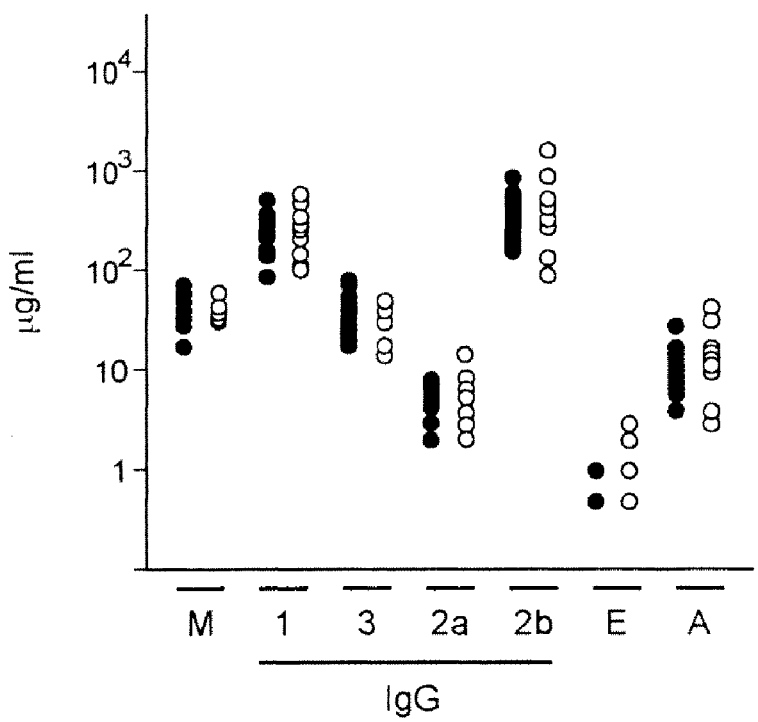
FIG. 7: Total serum immunoglobulin levels IL-23p19$^{-/-}$ mice. Serum levels of immunoglobulin isotypes were determined by isotype specific ELISA from groups of 16 wild type (filled circles) and IL-23p19$^{-/-}$ (open circles) mice. Immunoglobulin isotypes are indicated at the bottom of the graph.

Humoral immune responses in IL-23p19$^{-/-}$ mice. To determine the role of IL-23 in the generation of a humoral immune response, first total immunoglobulin levels of all isotypes were measured in serum of 16 mice of either genotype. There was no statistically significant difference between wild type and IL-23p19$^{-/-}$ mice (FIG. 7), indicating that the IL-23 is not critically required for the maintenance of normal immunoglobulin levels. Next, we tested whether IL-23 is involved in the generation of a T-dependent humoral response against a protein antigen delivered in adjuvant. To this end, groups of 7 mice were immunized, each with Ovalbumin (OVA), and assessed OVA-specific immunoglobulin isotypes in preserum (all negative, data not shown), and after each of two consecutive immunizations (FIG. 8). After primary immunization, none of the groups differed from each other significantly for OVA specific IgG1, IgG2b, IgG3, and IgE. However, significantly reduced levels of OVA specific IgG2a and IgA in IL-23p19$^{-/-}$ and IL-12p40$^{-/-}$ animals were observed after primary immunization. As expected, the levels of all isotypes were increased dramatically after the second immunization. At this point, both IL-23p19$^{-/-}$ and IL-12p40$^{-/-}$ mice displayed marked reduction of all isotypes tested. The difference between these two genotypes was generally not significant, indicating that endogenous IL-12 does not play a major role in the humoral response in the absence of IL-23.

Figure 9:
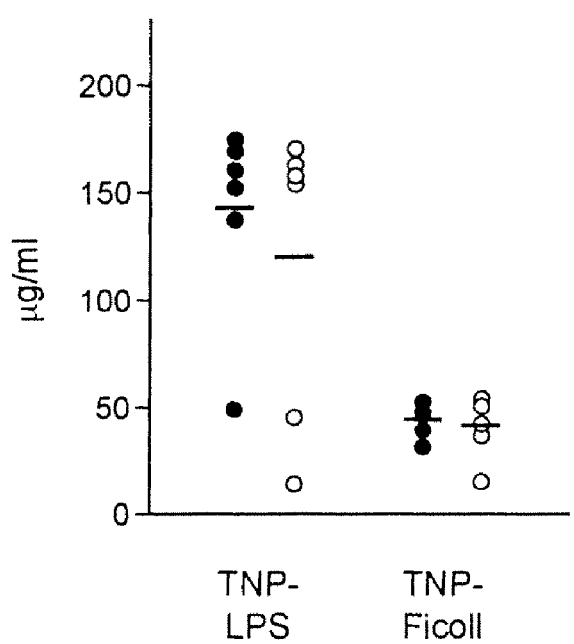
FIG. 9: T-independent B-cell responses are normal in IL-23p19$^{-/-}$ mice. Serum levels of TNP specific IgM was determined by ELISA from mice immunized with TNP-LPS (type I, left) or TNP-Ficoll (type II, right). Filled circles, wild-type mice; open circles, and IL-23p19$^{-/-}$ mice.

Because humoral immune responses depend of the proper function of both B and T cells, we next sought to determine by what mechanism IL-23 exerts its stimulatory effects. To test whether B-cell function is directly affected by the lack of IL-23, we tested the ability of IL-23 deficient mice to mount B-cell responses against T-independent (TI) antigens. The TI-1 antigen trinitrophenyl- (TNP-) LPS leads to B-cell activation via CD14 and TLR4, while the TI-2 antigen TNP-Ficoll activates B-cells through clustering of surface B-cell receptors. IL-23p19$^{-/-}$ mice mounted normal B-cell responses to both types of antigens (FIG. 9), indicating that IL-23 does not play a role in T-independent B-cell responses. Furthermore, B-cells from IL-23p19$^{-/-}$ mice proliferated normally in vitro in response to LPS, anti-IgM, and anti-CD40 and underwent normal isotype switching in response to IL-4 (not shown). IL-23 stimulation of B-cells did not lead to increased proliferation or isotype switching (not shown), and thus we conclude that IL-23 does not directly affect B-cell function.

Figure 10A:
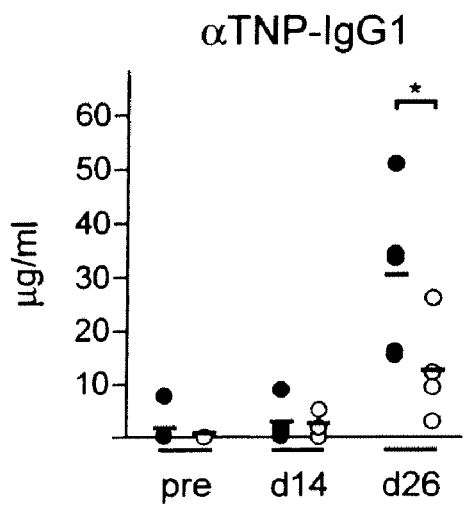
FIG. 10: Memory T-cell function. Wild type (filled circles) and IL-23p19$^{-/-}$ mice (open circles) were immunized on day 0 with Ovalbumin and challenged on day 21 with TNP-OVA. Serum was harvested on days 0, 14, and 26 and tested by ELISA for the presence of TNP-specific IgG1 (A) and IgG2a (B). For IgG1, a commercially available standard was used. For IgG2a, arbitrary units were calculated as described in methods and materials.
Figure 10B:
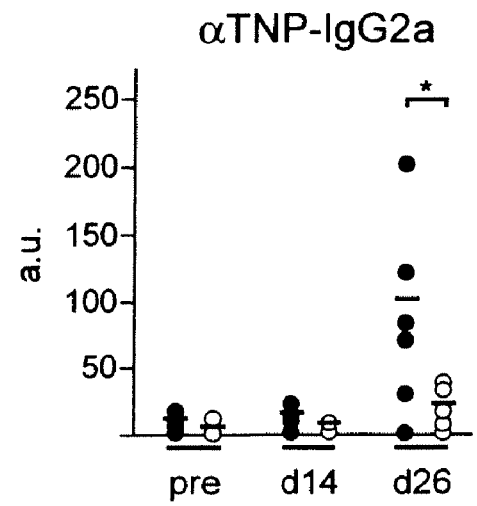

Because the humoral immune response was mainly compromised at the stage of the secondary immunization, and because B-cell function appeared normal in IL-23p19$^{-/-}$ mice, we hypothesized that inefficient re-activation of antigen specific helper T-cells might cause the phenotype. To address this question more directly, we immunized groups of 5-6 mice with OVA on day 0, followed by a secondary immunization with TNP conjugated OVA on day 14. By using this immunization regimen, memory T-cells specific for OVA are re-activated by the secondary immunization, but a novel set of B-cells with specificity for TNP is activated at the secondary time point only. Therefore, the OVA specific memory B-cell subset does not contribute to the formation of TNP-specific immunoglobulins. Seven days after the booster, we tested for TNP specific IgG1 and IgG2a in the serum, and found both isotypes to be significantly reduced in IL-23p19$^{-/-}$ mice (FIGS. 10A, B). This result further underlines the importance of IL-23 in T-dependent B-cell responses.

Figure 11:
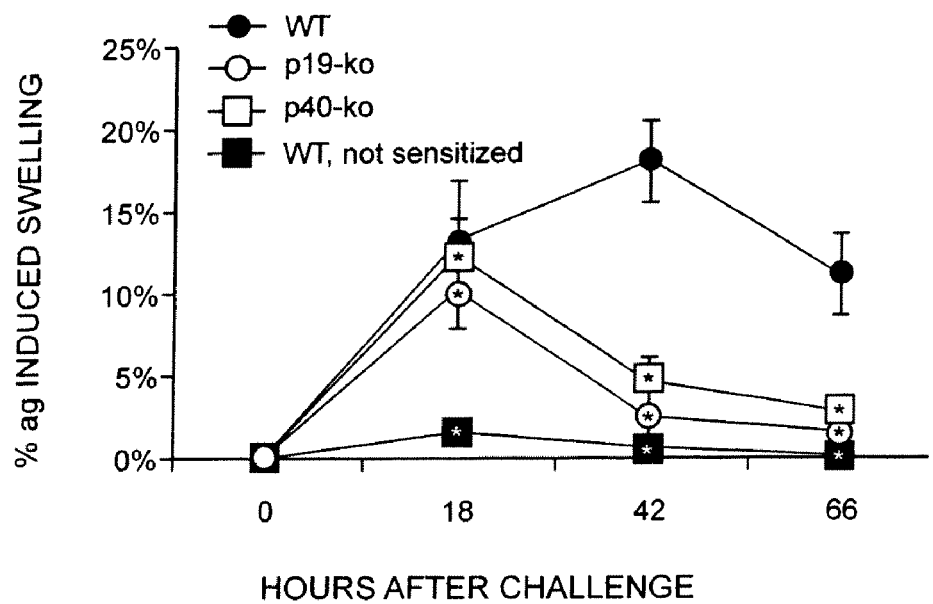
FIG. 11: Delayed type hypersensitivity (DTH) reactions. Antigen specific swelling is calculated as percent increase in footpad thickness over the value measured just before the challenge. The results were averaged over all six mice in each group, and error bars represent the standard deviations. A second wild-type group that was not sensitized is used as a control for swelling induced by the antigen alone. An asterisk inside a symbol indicates that the difference between the corresponding group and wild-type mice is statistically significant (P<0.05). WT, wild type; p19ko, IL-23p19$^{-/-}$ mice; p40ko, IL-12p40$^{-/-}$ mice.

Delayed type hypersensitivity (DTH) responses in IL-23p19$^{-/-}$ mice. To further investigate the function of memory CD4$^+$ cells in IL-23p19$^{-/-}$ mice, the ability of these animals to mount DTH responses was evaluated. DTH responses are strongly T-cell dependent and were reported to be defective in IL-12p40$^{-/-}$ mice, but appear to be normal in mice lacking IL-12p35, suggesting that they might be mediated by IL-23. To address this question, we sensitized groups of 6 wild-type, IL-23p19$^{-/-}$, and IL-12p40$^{-/-}$ animals each with methylated BSA (mBSA) in complete Freund's adjuvant (CFA) and elicited DTH responses 7 days later by injection of mBSA into footpads. To control for nonspecific swelling, we also challenged a group of wild-type mice that had not been sensitized. Specific footpad swelling was measured 18, 42, and 66 hours after the challenge and found to be inhibited to a similar degree in both IL-12p40$^{-/-}$ and IL-23p19$^{-/-}$ mice compared to wild-type mice (FIG. 11). The kinetics was also similar, with both IL-12p40$^{-/-}$ and IL-23p19$^{-/-}$ mice showing strongly reduced swelling at the 42 and 66 but not at the 18 hour time point. Therefore, IL-23 is a principal mediator of DTH responses, and lack of IL-23 leads to inefficient responses by memory CD4$^+$T-cells.

Figure 12A:
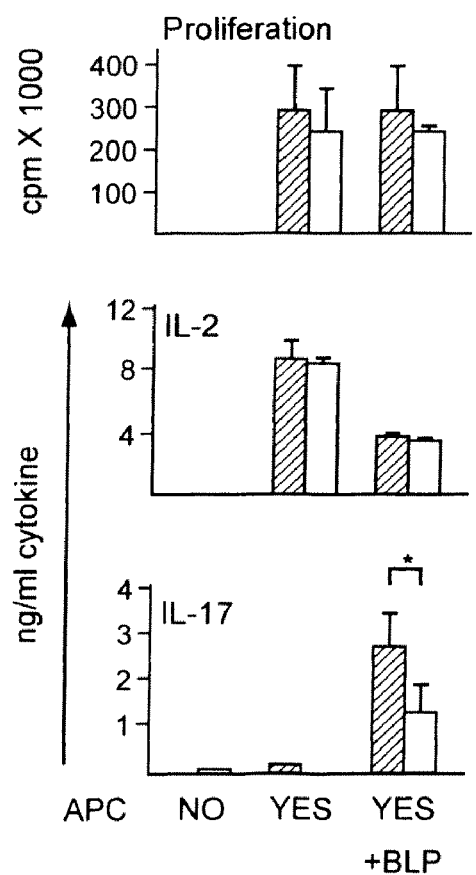
FIG. 12: Normal T-cell priming yet reduced levels of IL-17 production by IL-23p19$^{-/-}$ antigen presenting cells. A: in vitro allostimulation experiment of balb/c T-cells in combination with wild-type (black bars) or IL-23p19$^{-/-}$ (white bars) dendritic cells. Naïve CD4$^+$ T-cells and CD8$^-$/CD11c$^+$/MHC-II$^+$ cells were isolated by FACS and incubated in the presence or absence of bacterial lipopeptides (BLP). Proliferation and cytokine levels in the supernatants were determined after a 5-day incubation period. APC, antigen presenting cells. B: In vivo T-cell response. Lymph node cell suspensions from wild-type (black bars) or IL-23p19$^{-/-}$ mice (white bars) immunized with KLH were isolated and restimulated in vitro with 25 µg/ml KLH. Proliferation and IL-17 levels were measured after 5 days in culture.
Figure 12B:
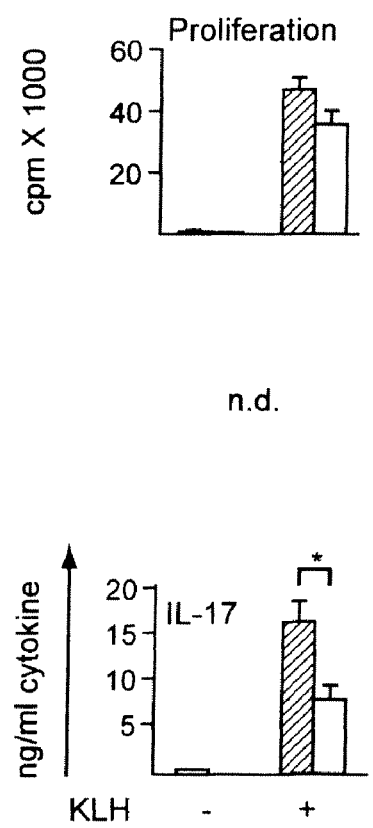

Capacity of IL-23p19 dendritic cells to stimulate T-cells. To rule out the possibility that the defects observed in IL-23p19$^{-/-}$ mice are due to inefficient T-cell priming by IL-23 deficient antigen presenting cells, we next investigated the potential of IL-23p19$^{-/-}$ DC to stimulate allotypic naïve CD4$^+$ T-cells isolated from the spleens of balb/c mice. In the absence of DC, these T-cells did not proliferate nor secrete appreciable amounts of cytokines (FIG. 12A). Addition of DC of either genotype resulted in robust proliferation and production of IL-2 in both genotypes. Since we have shown previously that IL-23 is a potent inducer of IL-17, we next induced IL-23 production by DC using bacterial lipopeptides, a potent Toll-like receptor- (TLR-) 2 agonist and inducer of IL-23 production. Under these conditions, wt DC potently induced IL-17 production by the T-cells (FIG. 12A, bottom panel), while T-cells stimulated with IL-23p19$^{-/-}$ DC produced significantly less IL-17. To confirm these observations in a more physiological setting, we next elicited T-cell responses in vivo by immunizing groups of 8 mice with Keyhole-limpet hemocyanin (KLH) in complete Freund's adjuvant (CFA). Draining lymph node cells (LNC) were harvested 5 days later and re-stimulated with KLH in vitro. Again, we observed that LNC harvested from IL-23p19$^{-/-}$ mice produced significantly less IL-17 (FIG. 12B, bottom panel). LNC proliferation was comparable in both genotypes (FIG. 12B, top panel), indicating that both wt and IL-23p19$^{-/-}$ mice mounted robust T-cell responses against the antigen. Thus, IL-23 deficiency does not grossly impair the stimulatory potential of dendritic cells, but results in attenuated IL-17 production by T-cells.

Discussion

Using IL-23p19 deficient mice, the non-redundant in vivo functions of IL-23 were assessed, and found that IL-23 deficiency results in compromised T-cell dependent immune responses, such as humoral immune responses and DTH reactions.

Profoundly reduced humoral immune responses were observed in IL-23p19$^{-/-}$ mice, affecting all immunoglobulin isotypes. In parallel, responses of IL-12p40$^{-/-}$ mice were inhibited to a similar or slightly higher degree. Our results support the conclusion that IL-23 is absolutely required for an efficient humoral response, while it remains to be determined, through the use of IL-12p35$^{-/-}$ mice, whether IL-23 is sufficient for normal humoral responses in the absence of IL-12.

In summary, IL23p19$^{-/-}$ mice have attenuated in vivo T-cell responses manifesting in reduced DTH and humoral immune responses, and phenotypically resemble IL-17 deficient mice. Our results indicate that clinical administration of IL-23 or its agonists might be beneficial to support T-cell function in immunization regimens and in immunocompromised patients.

While the present invention has been described with reference to what are considered to be the specific embodiments, it is to be understood that the invention is not limited to such embodiments. To the contrary, the invention is intended to cover various modifications and equivalents included within the spirit and scope of the appended claims.

What is claimed is:

1. A method for treatment of an inflammatory disease in a human subject comprising measuring the expression level of interleukin-17 (IL-17) in said subject, and, if the IL-17 expression level is determined to be elevated, treating said subject with an effective amount of an anti-interleukin-23 (anti-IL-23) antibody or an anti-IL23 receptor antibody.

2. The method of claim 1 wherein said antibody is an antigen-binding fragment.

3. The method of claim 2 wherein said antigen-binding fragment is selected from the group consisting of Fv, Fab, Fab', and $F(ab')_2$.

4. The method of claim 1 wherein said antibody is a full-length antibody.

5. The method of claim 1 wherein said antibody is chimeric.

6. The method of claim 1 wherein said antibody is humanized.

7. The method of claim 1 wherein said antibody is human.

8. The method of claim 1 wherein said antibody inhibits the ability of IL-23 to induce IL-17 production in activated T cells.

9. The method of claim 1 wherein said inflammatory disease is selected from rheumatoid arthritis (RA), multiple sclerosis (MS), asthma, systemic lupus erythrematosus, Behcet's disease, and psoriasis.

10. The method of claim 9 wherein said inflammatory disease is RA, MS or asthma.

* * * * *

UNITED STATES PATENT AND TRADEMARK OFFICE
CERTIFICATE OF CORRECTION

| | | |
|---|---|---|
| PATENT NO. | : 8,287,869 B2 | Page 1 of 1 |
| APPLICATION NO. | : 12/350125 | |
| DATED | : October 16, 2012 | |
| INVENTOR(S) | : Gurney | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 399 days.

Signed and Sealed this
Twenty-third Day of September, 2014

Michelle K. Lee
*Deputy Director of the United States Patent and Trademark Office*

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gcttggtggc ccacctatga t                                              21

<210> SEQ ID NO 2
<211> LENGTH: 20
<212> TYPE: DNA
<213> ORGANISM: Artificial Sequence
<220> FEATURE:
<223> OTHER INFORMATION: Sense primer

<400> SEQUENCE: 2
agaccctcaa agttcatgac                                                20
```

```
<210> SEQ ID NO 3
<211> LENGTH: 20
<212> TYPE: DNA
<213> ORGANISM: Artificial Sequence
<220> FEATURE:
<223> OTHER INFORMATION: Antisense primer

<400> SEQUENCE: 3
ctgacggcgc tttctctacc                                               20

<210> SEQ ID NO 4
<211> LENGTH: 20
<212> TYPE: DNA
<213> ORGANISM: Artificial Sequence
<220> FEATURE:
<223> OTHER INFORMATION: Sense primer

<400> SEQUENCE: 4
ttttgccagt gggatacacc                                               20

<210> SEQ ID NO 5
<211> LENGTH: 20
<212> TYPE: DNA
<213> ORGANISM: Artificial Sequence
<220> FEATURE:
<223> OTHER INFORMATION: Antisense primer

<400> SEQUENCE: 5
aactgctggg gctgttacac                                               20

<210> SEQ ID NO 6
<211> LENGTH: 20
<212> TYPE: DNA
<213> ORGANISM: Artificial Sequence
<220> FEATURE:
<223> OTHER INFORMATION: Common antisense primer

<400> SEQUENCE: 6
gcctgggctc acttttctg                                                20

<210> SEQ ID NO 7
<211> LENGTH: 20
<212> TYPE: DNA
<213> ORGANISM: Artificial Sequence
<220> FEATURE:
<223> OTHER INFORMATION: Wild-specific specific sense primer

<400> SEQUENCE: 7
gcgtgaaggg caaggacacc                                               20

<210> SEQ ID NO 8
<211> LENGTH: 20
<212> TYPE: DNA
<213> ORGANISM: Artificial Sequence
<220> FEATURE:
<223> OTHER INFORMATION: Knockout specific sense primer

<400> SEQUENCE: 8 aggggagga ttgggaagac                                                20
```